United States Patent
Liu

(10) Patent No.: US 9,250,230 B2
(45) Date of Patent: Feb. 2, 2016

(54) USING INDUCED PLURIPOTENT STEM CELLS FOR SCREENING ANTI-NEOPLASTIC AGENTS

(71) Applicant: Shi V. Liu, Apex, NC (US)

(72) Inventor: Shi V. Liu, Apex, NC (US)

( * ) Notice: Subject to any disclaimer, the term of this patent is extended or adjusted under 35 U.S.C. 154(b) by 0 days.

(21) Appl. No.: 13/957,423

(22) Filed: Aug. 1, 2013

(65) Prior Publication Data

US 2014/0134667 A1    May 15, 2014

Related U.S. Application Data

(63) Continuation-in-part of application No. 12/931,439, filed on Feb. 1, 2011, now abandoned.

(51) Int. Cl.
*G01N 33/50* (2006.01)

(52) U.S. Cl.
CPC ........ *G01N 33/5011* (2013.01); *G01N 33/5073* (2013.01)

(58) Field of Classification Search
None
See application file for complete search history.

(56) References Cited

U.S. PATENT DOCUMENTS

2010/0255471 A1* 10/2010 Clarke et al. ............. 435/6
2011/0301153 A1* 12/2011 Thompson et al. ...... 514/224.8

OTHER PUBLICATIONS

Liu, S., iPS Cells: A More Critical Review; Stem Cells and Development, vol. 17, pp. 291-297, 2008.*

* cited by examiner

*Primary Examiner* — Addison D Ault
(74) *Attorney, Agent, or Firm* — Dentons US LLP

(57) ABSTRACT

The invention uses induced pluripotent stem cells (iPSCs) for screening anti-neoplastic agents by examining the capability of a single agent, compound or drug, or a combination of multiple agents, compounds or drugs, for inhibiting or suppressing one or more neoplastic activities or processes, including aerobic glycolysis and neoplastic anabolism and, thus, inhibiting rapid growth and excessive reproduction of neoplastic cells. Agents, compounds or drugs may also be screened for their potential in inhibiting an invasion and/or migration of neoplastic cells into healthy or normal tissues and/or cells and a metastasis of neoplastic cells into other sites of the body. Anti-neoplastic agents, compounds and/or drugs found through these methods may represent broad-spectrum anti-neoplastic agents, compounds and/or drugs that preferentially target and damage neoplastic tumor or cancer cells but exert limited or minimal harm to normal or healthy cells.

15 Claims, No Drawings

USING INDUCED PLURIPOTENT STEM CELLS FOR SCREENING ANTI-NEOPLASTIC AGENTS

CROSS REFERENCE TO RELATED APPLICATIONS

This patent application is a continuation-in-part application of pending non-provisional patent application U.S. Ser. No. 12/931,439 of Shi V. Liu, filed on Feb. 1, 2011, entitled "Using Cells Reprogrammed with Oncogenic Factors for Screening Anti-Neoplastic Agents." This continuation-in-part patent application claims the benefit of priority to non-provisional patent application Ser. No. 12/931,439, filed on Feb. 1, 2011, which patent application is hereby incorporated into this continuation-in-part patent application in its entirety by reference herein, including all parts thereof and each of its originally-filed claims.

TECHNICAL FIELD

The present invention relates to unique methods for screening agents that are potentially effective in partially or fully inhibiting neoplastic aerobic glycolysis and/or anabolism supporting excessive cell reproduction, and in reducing an invasion and/or migration of neoplastic cells into healthy or normal tissues or cells of human beings and/or animals (or other mammals). More specifically, the invention utilizes induced pluripotent stem cells (iPSCs) as a means or tool for screening one or a plurality of agents, compounds and/or drugs that may potentially specifically inhibit neoplastic aerobic glycolysis and/or anabolism, as well as the invasive and/or metastatic properties of neoplastic cells.

TERMS AND DEFINITIONS

For purposes of clarity, various terms and phrases used throughout this specification and the appended claims, which are identified below in bolding, are defined in the manner set forth below. If a term or phrase used in this specification, or in the appended claims, is not defined below, or otherwise in this specification, the term or phrase should be given its ordinary meaning.

About and Approximate as are used herein mean approximately, as is known, and may be determined, by those having ordinary skill in the art, and typically includes a variation of a numeric value described herein by ±0.2.

Addiction as is used here means a state of being dependent on something or a preference for something. For example, glutamine addiction in tumor/cancer cells refers to the dependency or preferential use of glutamine for support the neoplastic anabolism in these cells.

Adult Stem Cells (ASCs) as is used here means stem cells found in the tissues of an adult body of human or animal.

Aerobic Glycolysis as is used herein means glycolysis in the presence of oxygen. This phenomenon was first observed in 1930s by Warburg in tumor cells which shows elevated glycolysis even in the presence of high-level of oxygen. This Warburg Effect has since been known as a hallmark of tumor/cancer cells.

Age and Aging as are used herein mean, respectively, the chronological time that an organism has experienced since its birth and the process that the organism looses its physical integrity and function capability over living time.

Agent as is used herein means a chemical, or a compound, or a substance, or a force, or an energy particle or a drug.

Anabolism as is used herein means a constructive metabolism in which living organisms build more complex substances from simple substances, usually requiring an energy input.

Anabolism is an opposite term to Catabolism.

Anaplasia as is used herein means the loss of structural differentiation within a tissue. Anaplasia is a characteristic of tumor/cancer tissue.

Anti-Cancer and Anti-tumor as are used herein mean, respectively the action against cancer and the action against tumor.

Anti-Neoplastic as is used herein means action against a neoplastic activity, capability, process, or a combination of them.

Apoptosis as is used herein means a normal, genetically regulated process leading to the death of cells. Apoptosis is also known as programmed cell death (PCD), as in contrast with necrosis which is a result of killing of cell due to infection and inflammation.

Benign as is used herein in connection with a neoplasm (mass of neoplastic cells) means the relative better preservation of the differentiation hierarchy in the tissue as compared with the anaplasia often seen in the malignant neoplasm. Benign tumors often show slower growth rate than malignant tumors and lack invasion capability of malignant tumors. Benign tumors rarely metastasize from primary location to remote locations in a body. Benign tumors are typically surrounded by an outer surface (fibrous sheath of connective tissue).

Broad-Spectrum as is used herein in connection with the capability of an agent, a compound, or a drug used for treating neoplasm (tumor or cancer) means the coverage of multiple types of neoplasms (tumors or cancers) within its effective range.

Cachexia as is used herein means a general ill health and weak body, usually occurring in association with a neoplastic disease or a chronic infection.

Cancer as is used herein means a malignant and invasive growth of tumor, especially one originating in epithelium, tending to recur after excision and often metastasize to other sites in the body.

Carcinogenesis as is used herein means development of cancerous cells from normal cells.

Cancer Cell is a cell that is part of a malignant tumor. Cancer Cell as is used herein generally means a cell that grows rapidly and reproduce excessively, shows low-level of cell differentiation, rarely undergoes apoptosis under normal conditions, and does not have functional "gap junctional intercellular communications" (GJICs), which are typically necessary for cell differentiation.

Catabolism as is used herein means destructive metabolism in which the more complex substances breaking down into simpler substances, usually with a release of energy through the generation of ATP, an energy-rich compound. Catabolism is an opposite term of Anabolism.

Cell as is used herein means the basic structural, functional and biological unit of all known living organisms, and can: (1) metabolize (transform substances and produce energy); (ii) reproduce (making offspring for species preservation of population proliferation or multiplication); (iii) differentiate (become specialized in order to perform a specific function); (iv) apoptose (die without releasing harmful substances into the surrounding area); (v) senesce (age and thus lose reproduction capability but remains alive and metabolically active); or (vi) adaptively respond to environmental stimulus. A cell is the smallest unit of life that is classified as a living thing. Cells consist of a protoplasm enclosed within a membrane which serves as an interface between intracellular and extracellular environments.

Cell Death as is used herein means the ending of cell life which is definitely shown as the cessation of active metabolism and the break apart of the cell body.

Cell Differentiation as is used herein means the specialization of a cell with more developmental potentials into a less developmental potential.

Cell Division as is used herein means a mistaken concept that incorrectly describes the Cell Reproduction as "one-mother-cell-divides-into-two-daughter-cells" and consequently places cell biology on a fundamentally wrong basis.

Cell Invasion as is used herein means the penetration of a cell across a barrier formed by the other cells. Possessing Cell Invasion capability is a characteristic feature of malignant tumor cells such as cancer cells. Cell Invasion Assays are assays for examining the cell invasion capability of cells and available from sources that are known by those having ordinary skill in the art, such as Cell Biolabs, Inc. (San Diego, Calif.).

Cell Migration as is used herein means a highly integrated, multi-step cell movement or translocation process that plays an important role in the progression of various diseases including cancer, atherosclerosis and arthritis. Cell Migration Assays are available from sources that are known by those having ordinary skill in the art, such as Cell Biolabs, Inc. (San Diego, Calif.).

Cell Reproduction as is used herein means the generation of next-generation offspring cell(s) by a mother cell. It was a discovery by the inventor of this invention back in 1990s that bacteria do not divide but reproduce that has challenged the "one-mother-cell-divides-into-two-daughter-cells" cell division dogma and thus established a correct basis for understanding cell life [214, 215]. In cell reproduction, the mother cell reproduces one or more offspring daughter cells and becomes older (in chronological age).

Cori Cycle as is used herein means the cycle in carbohydrate metabolism consisting of the conversion of glycogen to lactic acid in muscle, diffusion of the lactic acid into the bloodstream which carries it to the liver where it is converted into glycogen, and the breakdown of liver glycogen to glucose which is transported to muscle by the bloodstream and reconverted into glycogen.

Cultivate and culture as are used herein mean a propagation of cells in media conducive to their growth and reproduction.

Component as is used herein means a part, portion, element, constituent or ingredient, and is used interchangeably with "ingredient" and "agent." For example, in connection with the methods of the invention, this term may mean an ingredient, or combination of ingredients, used in these methods, or a part, portion, element or constituent thereof, depending upon the context in which this term is used, which may readily be determined by those having ordinary skill in the art.

Development as is used herein means the formation from a totipotent zygote cell a multicellular body with various organs consisting of tissue cells in various degrees of cell differentiation. Differentiation as is used herein means the specialization of daughter cells reproduced from a mother cell.

Effective as is used herein in connection with an ingredient, composition, agent, compound, drug and/or the like, in many instances, and depending upon the context, as may be determined by those having ordinary skill in the art, means that the ingredient, composition, agent, compound, drug and/or the like has or provides one or more of the qualities, characteristics and/or benefits that are described herein, either partially (greater than 0% but less than 100%) or fully (100%), such as inhibiting neoplastic activity.

Elevation as is used herein means the increase of something like the activity of an enzyme, or the concentration of a substance. The degree of Elevation is usually in a relative comparison between a basic state and an excited state or between a control group without and a treatment group with something like an agent, a compound or a drug.

Embryonic Stem Cells (ESCs) as is used herein means the stem cells existing in the embryonic body of an organism.

Embryogenesis as is used herein means the process by which the embryo is formed. Embryogenesis starts from a zygote cell which forms as a result of the fertilization of an ovum (egg) by a sperm and ends up with the formation of a fetus.

Epigenetic, Epigenetics and Epigenome as are used here mean respectively the involvement of a modification in gene expression that is independent of the DNA sequence of a gene; the study of heritable changes in gene function that do not involve changes in DNA sequence; the network of chemical compounds surrounding DNA that modify the genome without altering the DNA sequences and influence expression of multiple genes in an organized fashion.

Epigenetic Landscape as is used herein means a metaphor describing the change in epigenomes over the development of a multicellular organism from a zygote. This term was originated by Conrad Hal Waddington who said that cell fates were established in development much like a marble rolls down to the point of lowest local elevation. Waddington suggested visualizing increasing irreversibility of cell type differentiation as ridges rising between the valleys where the marbles (cells) are travelling.

Extracellular Acidification Rate (ECAR) as is used herein means the rate of proton production as a result of glycolysis.

Excessive as is used herein means more than is typical or normal as is reasonably measured using methods that are known by those having ordinary skill in the art.

Excessive Reproduction or Excessive Cell Reproduction as are used herein mean abnormal speed of cell reproduction. It is a characteristic of neoplastic cells which usually have a higher capability than normal cells in utilizing substrates more for anabolism than for catabolism and thus supporting the cell growth and cell reproduction.

Exogenous as is used herein means "outside" and refers to an action or object coming from outside of a system, such as a cell. Exogenous Genes as used herein means genes taken from other cells and placed into a recipient cell.

Full and Complete as are used herein mean 100% or near 100% such as over 95%.

Gene, Genetic, Genetics as are used herein mean respectively a specific sequence of nucleotides in DNA or RNA that is located usually on a chromosome and that is the functional unit of inheritance controlling the transmission and expression of one or more traits by specifying the structure of a particular polypeptide and especially a protein; a feature relating to, caused by, or controlled by a gene; and the genetic makeup and phenomena of an organism or the study of genetic makeup and phenomena.

Genome and Genomics as are used herein mean respectively one haploid set of chromosomes with the genes they contain or, more broadly, the genetic material of an organism and a branch of biotechnology concerned with applying the techniques of genetics and molecular biology to the genetic mapping and DNA sequencing of sets of genes or the complete genomes of selected organisms using high-speed methods, with organizing the results in databases.

Germ Cell and Germ Line as are used here mean a gamete (as an egg or sperm cell) or one of its antecedent cells and the cellular lineage of a sexually reproducing organism from which eggs and sperm are derived.

Glycolysis as is used herein means the enzymatic breakdown of a carbohydrate (as glucose) by way of phosphate derivatives with the production of pyruvic or lactic acid and energy stored in high-energy phosphate bonds of ATP, Glycolysis takes place in all proliferating cells, especially in neoplastic tumor/cancer cells.

Glutaminolysis as is used herein means a series of biochemical reactions by which the amino acid glutamine is degraded to glutamate, aspartate, $CO_2$, pyruvate, lactate, alanine and citrate. Glutaminolysis takes place in all proliferating cells, especially in neoplastic tumor/cancer cells.

Growth as is used herein means the increase in size, mass, weight or the combination of them in an individual cell or organism.

Heredity and Inheritance as are used herein mean the sum of the characteristics and potentialities derived from one's ancestors and the transmission of such qualities from ancestor to descendant. In the past only genetic features are known as inheritable heredity. But recently epigenetic features have also been shown as inheritable heredity.

Humans as is used herein, unless otherwise stated, includes human beings that are babies, infants, children or adults.

Hypoxia as is used herein means a deficiency of oxygen reaching the tissues of the body.

Induced Pluripotent Stem (iPS) Cells (iPSCs) as are used herein mean a variety of pluripotent stem cells obtained from tissue cells that are cultivated in vitro and artificially manipulated via a processes known as "reprogramming".

Influencing as is used herein mean having an impact on something.

Ingredient as is used herein may be used interchangeably with "component" and "agent" in connection with the methods described herein.

Inhibiting, Inhibitory and Suppressing as are used herein means partially (less than 100%) or fully (100%) reducing or stopping.

Invasion as is used herein means an infiltration and/or destruction of surrounding tissue, and is characteristic of malignant tumors.

iPS as is used herein means induced pluripotent stemness.

iPS Reprogramming as is used herein means a process in which tissue cells are treated with "reprogramming factors" so their status is changed.

Malignant as is used herein means having the properties of anaplasia, invasiveness, and/or metastasis. Malignant is a term opposite to Benign.

Malignant transformation as is used herein means a transformation of normal cells into tumor or cancer cells.

Mammals as are used herein include humans and non-human mammals, such as animals (dogs, cats, horses, cows, bulls, pigs, goats, sheep, birds, fowl, or the like)).

Metabolism as is used herein means the sum of the processes in the buildup and destruction of protoplasm; specifically: the chemical changes in living cells by which energy is provided for vital processes.

Metabolome as is used herein means the complete set of small-molecule metabolites (such as metabolic intermediates, hormones and other signaling molecules, and secondary metabolites) to be found within a biological sample, such as a single cell, a group of cells, or a whole organism, Metastasis as is used herein means a transfer of disease from one organ or part of the body to another organ or part of the body that is not directly connected with it, due either to transfer of pathogenic microorganisms or to transfer of cells. All malignant tumors are typically capable of metastasizing.

Migration as is used herein means a movement of, for example, cells from one location to another location.

Multipotent Stem Cell or Adult Stem Cell as is used herein means a cell that is further committed to produce limited cell types, and is derived from a "pluripotent stem cell" during development. Such cells have been identified in both animal and human somatic tissues.

Mutagenesis as is used herein means the occurrence or induction of mutation.

Mutation as is used herein means a change. In conventional sense, it usually means a change in genetic material, especially the nucleotide sequence of the genome of an organism or extrachromosomal genetic element. In a broad sense, mutation can also refer the change in metabolism. Thus, Metabolic Mutation, Metabolic Alteration and Metabolism shift are used herein to describe a change in metabolic activity and metabolite profile. Oncogenic Metabolism and Oncogenic Metabolite (Oncometabolite) as are used herein mean metabolic activity that is inductive for oncogenesis and the metabolite characteristic for oncogenic metabolism.

Neoplasia as is used herein means the abnormal proliferation of cells which means the reproduction of these cells exceeds, and is uncoordinated with, that of the normal tissues around them.

Neoplasm as is used herein means an abnormal mass of tissue resulted from neoplasia. It is an abnormal new growth of cells or tissue that typically grows by cellular proliferation more rapidly than normal, continues to grow after the stimuli that initiated the new growth cease, shows partial or complete lack of structural organization and functional coordination with normal tissue, and usually forms a distinct mass of tissue which may be either benign or malignant. It may appear as tumor or cancer. Tumor represents a localized swelling formed by a solid neoplasm. Cancer represents a disease in which the neoplastic cells displayed not only uncontrolled growth (reproduction) but also invasion (intrusion on and destruction of adjacent tissues) and sometimes metastasis (dispersion to other locations in the body via lymph or blood). Neoplasm can be benign or malignant. Benign neoplasm often contains highly differentiated cells. Malignant neoplasm such as cancer often contains poorly differentiated or undifferentiated cells.

Neoplastic Activity as is used herein mean any activity that contribute to the formation, the growth, and the reproduction of a neoplastic cell.

Neoplastic Aerobic Glycolysis as is used herein means aerobic glycolysis more prominently occurs in neoplastic cells.

Neoplastic Anabolism as is used herein means anabolism contributing to the formation, growth, and reproduction of neoplastic cells Neoplastic Capability as is used herein means the capability of neoplastic cells to invade, migrate, and metastasize.

Neoplastic Cells as are used herein mean cells that are part of a tumor or a cancer.

Neoplastic Process as is used herein means a biological process in which cells reproduce uncontrollably. If the new cells remain clustered together, the tumor is typically said to be benign. However, if its cells have an ability to invade surrounding tissue, the tumor is typically said to be malignant or cancerous.

Neoplastic Transformation as is used herein means a conversion of normal cells into tumor or cancer cells.

Neoplastic Metabolism as is used herein means the sum of metabolism collectively contributing to the abnormal growth and reproduction of neoplastic cells such as tumor cells and cancer cells.

Normal Cells as is used herein means cells that are not diseased or defective.

Oncogene and Oncogenic Factor as are used herein mean a gene and a non-genetic factor which contributes to the formation of a tumor or a cancer.

Oncogene-Induced Senescence (OIS) as is used herein means a phenomenon observed in studying the effect of oncogene in benign tumor cells which shows "senescence" after oncogene treatment. The mechanism of OIS remains elusive even though it appears to be related to the action of tumor-suppressing factors.

Oncogenesis as is used herein means the induction or formation of tumors.

Oncogenic Metabolism as is used herein means the sum of metabolic changes inductive for the formation of tumor or cancer.

Oxidative Phosphorylation (OXPHOS) used as is herein means the synthesis of ATP by phosphorylation of ADP for which energy is obtained by electron transport and which takes place in the mitochondria during aerobic respiration.

Oxygen Consumption Rate (OCR) as used herein means a measurement of speed or level of the oxygen consumption during Oxidative Phosphorylation (OXPHOS).

Partial as is used herein means more than 0% and less than 100%, such as 1, 2, 3, 4, 5, 10, 15, 20, 30 and so forth.

Plurality as is used herein means more than one, such as two, three, four, five, six, seven, eight, nine, ten, eleven, twelve, thirteen, fourteen, fifteen, twenty, twenty-five, thirty, thirty-five and so forth.

Pathological Cori Cycle as is used herein means the flow of lactate from tumor or cancer cells to liver and then a return of glucose from liver to tumor or cancer cells for neoplastic anabolism.

Pluripotent Stem Cell as is used herein means a cell possessing developmental potentials of forming all cells in a body of a multicellular organism.

Potency and Developmental Potential as are used herein mean the capability of a cell to differentiating into other cell types upon differentiating cell reproduction. The hierarchy of potency include totipotent, pluripotent, multipotent, oligopotent, and unipotent. Totipotent stem cells can differentiate into embryonic and extraembryonic cell types. Pluripotent stem cells are the descendants of totipotent cells and can differentiate into nearly all embryonic cell, i.e. contributing to any cell into the three germ layers. Multipotent stem cells can differentiate into a number of cells, but only those of a closely related family of cells. Oligopotent stem cells can differentiate into only a few cells, such as lymphoid or myeloid stem cells. Unipotent cells can produce only one cell type, their own.

Preferential as is used herein means a tendency for and a choice for.

Proliferation as is used herein means the reproduction of cell.

Rapid Cell Growth and/or Reproduction as is used herein means cell growth and/or reproduction that occurs at a rate of speed that is greater than normally shown which can be measured by methods that are known by those having ordinary skill in the art, such as via cell proliferation assays to measure the cell doubling time in the cell culture.

Reproduction as is used here mean the creation of another individual of the next generation by an individual in an earlier generation.

Reprogramming as is used herein means an artificial process by which the state and the fate of a cell is changed.

Reprogramming Factors as are used here mean any factor, being a macromolecule or a small molecule, used in the Reprogramming.

Safe and Safety for use as is used herein in connection with an anti-neoplastic agent, compound or drug, and/or the like, means that the anti-neoplastic agent, compound or drug, and/or the like, and components contained therein, and methods for using them, using reasonable quantities, and administered for reasonable periods of time (such as recommended for a particular mammal by a physician, veterinarian or other skilled clinician), which may vary for different types of mammals, do not cause, or present an unreasonable risk of harm, damage, defect, disorder, deformity or injury to, or by, an average mammal, whether or not the mammal has one or more disorders, diseases, conditions or maladies.

Screening as is used herein means identification or discovery.

Self-Renewal is a misnomer incorrectly used for describing the persistent stay of a mother cell after it reproduces its daughter cell. Self-Renewal has been criticized as a kind of "self-cheating" because it mistakenly identified an even older mother cell after its cell reproduction as a "rejuvenated" baby cell based on the invalid cell division dogma.

Side Effect as is used herein means any effect of an agent, compound, drug or other medicine that is in addition to its intended effect, especially an effect that is harmful or unpleasant. Examples of side effects include, but are not limited to, inducing birth defects that would not otherwise occur, causing a new type of cancer or a toxicity in a patient and/or causing a "stress response" that functions to protect, rather than destroy, cancer cells, and/or the like.

Senescent and Senescence as are used herein mean the non-reproductive and the state of being non-reproductive.

Survival and Survival Rate as are used herein mean the state of remaining alive and the percentage of individuals in a population remaining alive for a given period of time.

Small-Molecule Compounds as are used herein means any non-macromolecules, typically those low molecular weight (<900 Daltons) organic compounds.

Somatic Cell as is used herein means any cell other than a "germ cell" (an ovum or sperm cell or one of their developmental precursors), and takes part in the formation of a multicellular organism, or an animal or human body, becoming differentiated into one of the various tissue cells.

Stem Cell as is used herein means a cell that has an ability to perform differentiating cell reproduction to produce daughter cells that have less developmental potency than itself has . . . Suppression Target as is used herein means aim or focus an action, plan of attack or attack at.

Terminally Differentiated Cell as is used herein means a cell that cannot perform any more cell-differentiating cell reproduction.

Totipotent Stem Cell as is used herein means a cell that can give rise to all cells of a complete multicellular organism. A sperm-"fertilized egg, the zygote, is a totipotent stem cell.

Transcription as is used here means the process of constructing a messenger RNA molecule (mRNA) using a DNA molecule as a template with resulting transfer of genetic information to the mRNA.

Transcriptome as is used herein means the set of all RNA molecules, including mRNA, rRNA, tRNA, and other non-coding RNA produced in one or a population of cells.

Transcription Factors as are used herein means proteins that bind to specific DNA sequences, thereby controlling the flow (or transcription) of genetic information from DNA to mRNA. Examples of transcription factors include, but are not limited to, Oct4, Sox2, Nanog, c-Myc, Ras, Kruppel-like factor 4 or Lin28, or any combination thereof.

Tumor and Tumorigenesis as are used here mean a mass of tumor cells and the process of forming the tumor.

Tumor Suppressor Genes as are used here mean genes involved in suppressing Tumorigenesis.

Viable and Viability as are used here mean being alive and the capability of remain alive.

Warburg Effect as is used herein means elevated glycolysis even in the presence of high-level of oxygen.

Weight Percent as is used herein refers to the percent weight, for example, of an ingredient that forms a part of a mixture, composition and/or the like, with the total weight of the mixture, composition and/or the like being 100 weight percent, and is a measure of the relative proportions of two or more quantities in a mixture Thus, weight percent may include any whole, partial, decimal or fractional number above 0, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 (or any amount in between the foregoing, such as 1.1, 1.2, 1.3, 1.4, 1.5, 1.6, 1.7, 1.8, 1.9 and so forth).

Wide-Spectrum as is used herein means a broad spectrum as defined earlier in connection with the capability of an agent, a compound, or a drug used for treating neoplasm (tumor or cancer) means the coverage of multiple types of neoplasms (tumors or cancers) within its effective range.

BACKGROUND OF THE INVENTION

Mutagenesis, Tumorigenesis and Carcinogenesis

Today's understanding of mutagenesis of human and animal cells that result in the formation of tumor (tumorigenesis) and cancer (carcinogenesis) is still far from complete. Two opposing hypotheses of the origin of tumor/cancer have existed for many decades. Although old and new hypotheses and observations coexist, in vitro and in vivo studies have not always been consistent, and there seems to be no clear resolution of how tumors/cancers really occur and what roles the genetic mutagenesis and the epigenetic alterations play in the origin and formation of tumors/cancers and how environmental factors affect the respective processes.

The tumorigenic/carcinogenic process in humans and animals appears to involve interactive roles of both genetic factors (tumor suppressor genes, proto-oncogenes, other genes) that direct cell behavior, errors in one or more of the various stages of DNA replication and the like and epigenetic factors that alter cell behavior by modifying on DNA "decorations" and change chromatin "structures". On top of these complex interplays between genetic and epigenetic factors in the origin and formation of tumors/cancers environmental factors (different physical or cultural environments, X-rays, ultraviolet radiation, mutagenic pollutants, tumor- or cancer-promoting chemicals and environmental toxicants, gender (hormones), diet and the like) also influence the tumorigenesis/ carcinogenesis during different stages of life development (maternal/embryonic, neonatal, adolescent, adult and senescent/geriatric). Thus, there is a huge need for further advance our knowledge on mutagenesis, tumorigenesis and carcinogenesis.

Tumor/Cancer Therapies

Current therapies and drugs for treating tumor/cancer have significant difficulties and are, and have been, relatively ineffective. Many tumors and cancers are not treated successfully. This may be because various drug therapies do not properly target the source of the tumor or the cancer, or that they have multi-drug resistance (due to a presence of one or more drug-resistant genes in the genomes of tumor/cancer cells). Also, various genes present in cancer cells and tumor cells are able to be turned "on" or "off." Moreover, there are many different types of tumor/cancer cell lines. Additionally, cells within a tumor/cancer are heterogeneous, rather than homogeneous, in nature. These cells represent a wide variety of genotypic and phenotypic characteristics. Further, no two tumors/cancers of a given origin in either an animal or a human being would contain tumor/cancer cells that are uniformly genetically and phenotypically identical. Moreover, as a tumor/cancer grows, the microenvironment within the tumor/cancer changes, which is caused by decreasing oxygen tension and blood nutrient availability. The tumor/cancer can also be influenced by the environmental factors that are described above, such as hormones and diet. Further, some tumor/cancer cells express drug-resistant genes. Still further, some anti-tumor/anti-cancer drugs, such as thalidomide, cause serious side effects, such as inducing birth defects that would not otherwise occur, causing a new type of tumor/cancer or a toxicity in a patient and/or causing a "stress response" that functions to protect, rather than destroy, cancer cells. Many of the foregoing explanations also explain discrepant or contrasting results that are often obtained from an experimental testing of a potential anti-tumor/anti-cancer drug in vitro as compared with in vivo. For example, typical cell cultures have a high-level of oxygen content as a result of both the culture media and the atmosphere, whereas tumors/cancers growing in an animal or human are typically not exposed to such oxygen-containing factors.

Medical Needs

There has been, and remains, a very significant long-felt, and unresolved, need in the tumor/cancer field for identifying and developing reliable broad-spectrum anti-tumor/cancer drugs and agents that: (i) are effective in killing a variety of tumor/cancer cells; (ii) do not kill or harm normal cells or tissues, which may be adjacent to tumor/cancer cells, the result of which could lead to the death of a patient; and (iii) do not have harmful, uncomfortable or other disadvantageous side effects. Presently existing anti-tumor/cancer drugs and agents typically do not possess each of these three characteristics, and tumor/cancer researchers have tried, and failed, to identify and develop such drugs and agents, which is very challenging for the reasons that are set forth above. Additionally, improper hypotheses, logic and approaches at the cellular level may have been employed by cancer researchers in an attempt to identify and develop such drugs and agents.

Shortcomings of Current Anti-Tumor/Anti-Cancer Drugs

Many conventional anti-neoplastic agents or anti-cancer drugs suffer from drawbacks of severe side effects due to their inhibition on some common processes shared by normal cells [1-3]. On the other hand, highly-specific anti-neoplasm drugs that target at the specific "leaf" level genetic mutation unique to different neoplastic cells are not only too narrow spectrum in their anti-neoplastic effect, but also suffer from losing effect as surviving neoplastic cells can develop resistance by using alternative routes [4-5]. More ironically, some anti-cancer agents can kill the targeted original cancer cells but, in the meantime, lead to the formation of new cancer in the patients [6-8]. The sad reality is that most anticancer drugs [9-10] really do not offer much meaningful benefit to patients' quality of life because they add just an extra week or two of suffering time to the patients' lifespan [11-12].

It turns out that the past as well as the current research on tumors and cancers have been focused too much on the distinct types of tumors and cancers in efforts for identifying their unique genetic mutations and thus develop highly specific anti-tumor/anti-cancer therapy. However, these scattered peripheral "leaf"-level hunting efforts for anti-tumor/anti-cancer drugs often meet with disappointments because many tumors/cancers have the capability of by-passing the very specific route targeted by those narrow-spectrum anti-tumor/anti-cancer drugs specifically designed for a "leaf"-level mutation. Therefore, there has been, and remains, a very significant long-felt, and unresolved, need in the tumor/cancer field for methods for reliably identifying broad-spectrum anti-tumor/cancer drugs that will target on the "root"-level process of tumors/cancers and thus cannot be by-passed by any tumor/cancer cell.

Neoplastic Metabolism: The Root-Process for all Neoplasms Including Tumors and Cancers The "root" of neoplasia or the "Achilles' heel" of neoplasm, which includes tumor and cancer, resides in the unique metabolic properties and the living processes of the neoplastic cells.

A hallmark of all neoplasms is their oncogenic metabolism, such as a high rate of glycolysis, even under a high oxygen concentration. This phenomenon has been known as the "Warburg Effect" since the 1930s, but remains poorly understood even today [14]. During aerobic glycolysis, pyruvate generated from glucose is not transported into mitochondria for total oxidation for yielding more energy but, rather, is converted to lactate in cytosol and then is excreted outside the cell [15]. For a long time, it was unknown why neoplastic cells would "waste" glucose and choose an energy-"inefficient" metabolism. However, the finding of a "neoplastic or pathological Cori cycle" in which the excreted lactate is carried by the blood to the liver and converted to glucose for reuse by the neoplasm may shed some light in understanding Cachexia, a condition exists in neoplastic patients who suffer massive loss of normal body mass as the neoplasm continues its growth [16]. It turns out that, by avoiding a complete "burn" of glucose to $CO_2$, neoplastic cells preserved some key carbon "skeleton" for neoplastic anabolism which represents another aspect of the oncogenic metabolism. The combined result of the "Warburg Effect" (the aerobic glycolysis) and the pathological "Cori Cycle" (the neoplastic anabolism) thus causes a metabolic imbalance: shifting resource toward neoplastic cells and away from normal cells. This metabolic imbalance ultimately results in systematic failure of patients suffering from a neoplastic disease and their death.

In addition, recent studies have shown that some of the molecular mechanisms underlying the neoplastic metabolism also influence invasion and migration of malignant neoplastic cells which are responsible for metastasis and a wider range of neoplastic diseases [17].

Needs for "Root"-Killing Broad-Spectrum Anti-Neoplastic Agents

Despite great progresses in understanding its etiology and pathology of neoplasia, neoplasm especially the malignant neoplasm such as cancer, still remains as a great risk to human life. Thus, an urgent need in combating neoplasia is to obtain some "root killers" for neoplastic cells [13]. In other words, we need to find wide-spectrum anti-neoplastic agents that are harmful for a variety of tumor/cancer cells but not harmful for normal or healthy cells.

Targeting Neoplastic Metabolism as the Achilles' Heel of Neoplasm

Neoplastic metabolism or tumorigenic/oncogenic metabolism is a common process that all tumor/cancer cells must rely on for their abnormal growth and excessive reproduction (multiplication or proliferation). The neoplastic metabolism or tumorigenic/oncogenic metabolism includes elevated aerobic glycolysis which is known as the Warburg Effect and enhanced neoplastic anabolism which is recognized as a pathological Cori Cycle. Thus, a very effective and much needed approach for treating neoplasia should be based on inhibiting aerobic glycolysis (Warburg Effect), neoplastic anabolism (pathological Cori Cycle), or both at the same time. This approach should yield therapeutic schemes that present much less (fewer) side effects than those associated with conventional anti-cell cycle (reproduction)-based therapy, such as "chemotherapy" or "radiotherapy." This approach should also yield much broader spectrum anti-neoplastic drugs than those approaches targeting at some rare mutations specific for only a certain type of neoplastic cells. Understanding unique metabolism common to all, or at least most, neoplastic cells and finding agents inhibiting such neoplastic metabolism may hit the Achilles' heel of neoplasm and eradicate neoplasm from its root.

The Shortage and Shortcomings of Primary Neoplastic Cells and their Cell Lines

In addition to the still lacking full translation of the existing insights into the causes of tumor/cancer from bench to bed, a major obstacle in searching for anti-neoplastic agents is ironically the shortage of neoplastic cells suitable for laboratory drug screening [18]. Despite the high incidence of neoplasia, neoplastic cells preserved for research use are relatively few. Collecting primary neoplastic cells is a complex procedure impeded with many red tapes, not to say the great investments and efforts required for characterizing them for research use. Consequently, only a limited number of primary cancer cells have been established as useful cell lines. Thus, there is a need to find more model neoplastic cells for utilization in screening anti-neoplastic agents.

In addition to this limitation in quantity, some neoplastic cell lines passed many times in the laboratories might have accumulated additional mutations that are atypical for natural neoplasm [18]. Thus, it is not uncommon that drugs effective against laboratory lines of cancer cells actually failed dramatically in clinical trials [19]. Some of the anti-cancer drugs actually lead to opposite effects [20-21]. It is also known that some conventional "chemotherapy" sometimes induces tumor regression while simultaneously elicits stress responses that protect subsets of tumor cells [22]. Thus, there is a need for finding more appropriate model neoplastic cells that are suitable for a reliable screening of anti-neoplastic agents.

In view of the above, it would be extremely beneficial to provide cost-effective and reliable methods for successfully discovering, identifying and/or screening for broad-spectrum (or other) anti-neoplastic agents, compounds and/or drugs that are safe for use by human beings and/or animals and may potentially have a therapeutic activity therein, such as partially or fully inhibiting a neoplastic activity or capability of neoplastic cells that are present in such human beings and/or animals, with minimal or no side effects.

Induced Pluripotent Stem Cells

Recently, cells known as induced pluripotent stem (iPS) cells (iPSCs) have been generated in large quantity and diversity [23-25]. The prototype iPSCs were first reported by Yamanaka's team in 2006 for mice [23] and in 2007 for human [24]. These iPSCs were claimed to be induced from differentiated cells by ectopic expressing exogenous transcription factors Oct4, Sox2, Klf4 and c-Myc [23-24] (abbreviated as OSKM) [123] and later known as Yamanaka factors [124]. Another group of iPSCs were reported in 2007 using Oct4, Sox2, Nanog, and LIN28 as the reprogramming factors [25] (abbreviated as OSNL) [123] and later known as Thomson factors [124].

These iPSCs have been described by others as "indistinguishable" from "embryonic stem cells" (ESCs) [26-28] and, thus, have been perceived as "ethical" and "safe" "replacements" of ESCs for cell therapy [29-31], and even for regenerative medicine [32-35].

Discovery: iPSCs are Man-Made Cancer Cells Due to Metabolic Mutation by iPS Reprogramming It is a discovery of the present inventor that iPSCs are incorrectly programmed stem cells (still abbreviated as iPSCs) or, in other words, man-made cancer stem cells (mmCSCs) [36-38]. Thus, iPSCs can be used as "replacements" for "naturally-occurring cancer cells" in screening agents against neoplastic cells.

It is a further discovery of the present inventor that iPS reprogramming can be linked with neoplastic aerobic glycolysis and anabolism [39]. Thus, iPSCs can be used as model cells for screening agents that specifically inhibit some aerobic glycolysis and anabolism characteristic for neoplasia.

In addition, it is a discovery of the present inventor that iPSCs may possess invasion and migration capability common to malignant neoplastic cells and, thus, may also be used for screening agents against the invasion, migration and metastasis of neoplastic cells.

Invention: Using iPSCs for Screening Anti-Neoplastic Agents for Broad-Spectrum Anti-Tumor/Anti-Cancer Drugs Based on the discovery of induced pluripotent stem cells (iPSCs) as man-made cancer cells an invention was made that iPSCs can be used for screening anti-neoplastic agents, compounds and drugs that are effective in inhibiting metabolic mutation which serves as a root for neoplastic transformation of normal cells into tumor/cancer cells.

This "odd" invention is apparently against the current mainstream thinking which regards iPSCs as "ethical" replacements for ESCs and "cancer-free" and, thus, even "safe" for cell therapy and regenerative medicine. However, it is right from those reports making "cancer-free" claims for iPSCs that the inventor of this patent application found evidence of the cancer risk for iPSCs [48]. With more detailed reasoning disclosed here for linking iPS reprogramming with neoplastic transformation, iPS researchers should come to a reality that their iPSCs may find a better utility: serving as serendipitous cancer cells for screening anti-neoplastic agents.

The Nonobvious Nature of the Invention

It should be pointed out that the present invention of using iPSCs for screening anti-neoplastic agents is fundamentally different from those inventions of using iPSCs as non-cancerous cells for modeling other diseases [40-41] and screening drugs against those diseases [42-43]. As a matter of fact, iPS researchers have been focused on inventing methods for making iPSCs [44] because human iPSCs have been perceived as "less complicated" "human pluripotent cells" than "embryonic stem cells" (ESCs) and thus are "potentially useful in therapeutic applications in regenerative medicine" [44]. More significantly, claims of generating "cancer"-free "safe" iPSCs suitable for clinical applications are being made repeatedly [28, 45-47], despite the criticisms against the hype contained in these claims [36, 48]. A very recent publication [49] describes acquisition of iPSCs by selecting those cells with transgenes integrated into the so-called "safe harbors," the genomic regions outside positions known for integration mutation. Even though the iPSCs are still made with the already known oncogenes, a claim of "out of harm's way" was still made [50]. This demonstrates the lack of understanding with regard to how iPS reprogramming results in neoplastic transformation and, thus, how similar iPSCs are to cancer cells than to ESCs.

It should be further pointed out that, even after the publication (on Aug. 2, 2012) of the parent patent application [125] of this patent application, the mainstream of iPSCs research still overlooked the discovery of epigenetic-level metabolic changes or metabolic mutations as the basis for the neoplastic nature of iPS reprogramming and the cancerous nature of the iPSCs. Most researchers are still hoping of creating "safe" iPSCs by eliminating genome-integration of the exogenous genes and removing integration remains of virus-vehicle [126-128]. New claims of creating "cancer-free" iPSCs or even "safer" iPSCs are continuously made [129-130]. At present time. mainstream iPS researchers and top journals are still rejecting the discovery of iPSCs as man-made cancer stem cells (mmCSCs) [37-38] which identifies some cancer risks for various "cancer-free" iPSCs [23-24, 26, 51-53]. Strong efforts are still being made in promoting iPSCs as "ethical" and "safe" ESC replacements for cell therapy and regenerative medicine [28, 54-58]. A recent publication reporting generating iPSCs from dermal fibroblasts of a patient suffering from Hutchinson-Gilford Progeria syndrome (HGPS) [59] has even been regarded as to "lead to novel insights into mechanisms of aging" [60], even though these HGPS-iPSCs are merely some cancerous cells carrying the mutations for HGPS.

Thus, even though some recent publications have noticed the "similarity" between iPSCs and cancer cells [61-62], or the common path between the generation of iPSCs and CSCs [63], the authors of these publications are still contributing the intriguing "parallel" as a result of partial [28] or incomplete [47] reprogramming. At the end, the intrinsic cancer risk of iPSCs has been neglected even in the "comprehensive review [28] or "straight talk" [47] by the leading iPS researchers. Arguments have also been made that "although there are common pathways activated during reprogramming and tumorigenesis, there are fundamental differences between iPS and transformed cancer stem cells" [63].

The awarding of a Nobel Prize in Physiology or Medicine to Yamanaka [131] is a strong indication that even the top scientists in the world still lack a minimal appreciation for the discovery of iPSCs as "man-made cancer stem cells" (mmCSCs) [36-39, 125], especially when this discovery was presented to the Nobel Prize selection committee [132]. Thus, it would not have been obvious at the time the present invention was made that iPSCs could be used for screening anti-cancer drugs when they are still considered as safe "replacements" of ESCs for cell therapy and even for regenerative medicine [133].

The non-obviousness of the deep insight on the intrinsic oncogenic and neoplastic transformation enabled with the iPS reprogramming is further evidenced by the rejection of the mainstream against the publication of the unique view by the inventor (see note in [39]) and the neglect of the prior art disclosed in the published patent application [125] by the mainstream. Some researchers in the field still tried to distinguish iPS reprogramming from oncogenesis and neoplastic transformation [134]. The fact is, there is no report of using iPSCs for screening anti-cancer drugs even after the publication of the patent application disclosing the invention of using iPSCs for screening anti-neoplastic agents, despite the strong need for developing anti-cancer drugs. Thus, even as today, the invention of using iPSCs for screening anti-neoplastic agents remains non-obvious even to the leading scientists in the related technical fields.

For example, a recent review published in Stem Cells and Development, which published a critical review on iPS cells in 2008, but later in 2009 rejected the submission of a manuscript describing cancer cell formation by iPS reprogramming (see note in [39]), considers "induced pluripotency and oncogenic transformation are related processes" [135]. It emphasizes more the "distinctions" between induced pluripotent stem cells (iPSCs) and oncogenic foci (OF) by stating that "iPSCs and OF shared a limited number of genes that were upregulated relative to parental fibroblasts" and "iPSCs and OF were distinct in that only iPSCs activated a host of pluripotency-related genes, while OF activated cellular damage and specific metabolic pathways" [135]. This review concludes that "OF and iPSCs are related, yet distinct cell types, and in which induced pluripotency and induced tumorigenesis are similar processes" [135].

The above view of treating iPSCs and OF as distinct cell types and separating iPS reprogramming from oncogenic transformation is incorrect because some of the differences between OF and iPSCs may be caused by the heterogeneous nature of OF due to the inherent variations in the differentiation status of the composing cells and the high purity of iPSCs as they are selected out based on some stemness markers [36]. However, that difference should not rule out the same oncogenic tumorigenesis or neoplastic transformation pathway used for forming OF and iPSCs. Indeed, using Nanog, a stemness marker and also a reprogramming factor used in some iPS reprogramming, reprogrammed oncogenic foci (ROF) with iPSC-like cells have been generated [135].

Evidences Supporting the Discovery and the Invention

Nevertheless, it is at least admitted by Yamanaka that iPSCs generated with his patented method have undeniable cancer risk as he recognized in his correction [137] to his Science publication [138] after thanking criticisms made by the inventor [139] of this invention [125]. Such risk was also confirmed by many later studies, including Yamanaka's own studies [87-89] The cancer risk may still exist for iPSCs generated with integration-free reprogramming methods [140, 141]. More convincingly, a Letter-to-the-Editor published in Stem cells showed that human induced pluripotent stem cells develop teratoma more efficiently and faster than human embryonic stem cells regardless the site of injection [142].

Interestingly, the unavoidable cancer risk associated with the prototype reprogramming method [136] has forced Yamanaka to file additional patent applications to claim "inventions" of selecting "safe" iPSCs [143,144]. However, these "inventions" are obvious responses to the public criticisms [36-39, 90-92, 125, 139, 141, 142, 168] made by the inventor of this patent application and actual implementations of some suggestions made in those public criticisms.

After all, the claims made in these patent applications may be invalid as the methods disclosed really lack any effective measure to overcome the intrinsic neoplastic nature of the iPS reprogramming and, thus, are really incapable of selecting cancer-free safe iPSCs [145].

Oncogenic Metabolism Resulted from Epigenetic Changes via iPS Reprogramming

The "root" cause for the neoplastic transformation via the iPS reprogramming is actually not the mutagenesis conventionally associated with random integration of exogenous genes and their vectors. It is some specific epigenomic alterations associated with the elevation of some specific reprogramming factors, as a result of introducing their genes, proteins, or RNAs, or even their metabolites or similar chemicals, into the recipient cells. The reprogramming factors have potent capability of activating the cell growth and reproduction of the recipient cells and, thus, make them highly proliferative. When such rapidly multiplying cells were selected out based upon some stemness markers, the so-called "induced pluripotent stem cells" (iPSCs) are obtained [36-39, 90-92, 125, 139, 141, 142, 168].

However, by clearly identifying the various linkages between iPS reprogramming and neoplastic transformation, it is hoped that the present application will establish a solid foundation for arguing iPSCs as a kind of "neoplastic" cells very similar to "natural" cancer cells and, thus, justifying their use as serendipitous "replacements" for cancer cells in methods for screening agents against neoplastic cells.

c-Myc and Lin28

It turns out that Myc (c-Myc), a very important iPS reprogramming factor, is a notorious oncogene and a master transcription factor that integrates cell proliferation with metabolism through its regulation of thousands of genes including microRNAs (miRNA) [64]. In addition to its known function in regulating the cell cycle and glucose metabolism [65], Myc also stimulates glutamine catabolism [66] through the repression of miRNAs miR-23a and miR-23b [67].

More significantly c-Myc enhances the expression of polypyrimidine tract binding protein PTB (also known as hnENPI), hnRNA1 and hnRNA2, and leads to selective expression of pyruvate kinase isoform 2 (PKM2) [65]. PKM2 is the M2 splice isoform of pyruvate kinase (PK) [68] which is a key enzyme for aerobic glycolysis [69], as compared with the M1 splice isoform of pyruvate kinase (PKM1) which is a key enzyme for oxidative phosphorylation. Thus, the selective expression of specific isoform of PK serves as a toggle switch for shifting mass-energy metabolism between an energy production-efficient oxidative phosphorylation and a mass production-efficient aerobic glycolysis.

It is interesting to notice that PKM2 is the dominant form of PK in "embryonic cells" and PKM1 is the dominant form of PK in the "adult cells" [68-69]. This age-specific expression of different isoforms of the same enzyme reflects the physiological need as PKM2 is needed for glycolytic anabolism supporting mass increase in the growth stage of the life, and PKM1 is needed for allowing established cells to perform more energy-consuming functions at the grown up stage of life. Thus, a change in the expression of different isoforms of the same enzyme leads to different modes of metabolism in different life stages. Overgrowth of cell mass, such as neoplasm, is not a desired shift.

Unfortunately, the re-expression of PKM2 [70] activates those "resting" cells and drives them from normally a "quiescent" state into a "hyper-proliferation" state [71]. This adulthood expression of an embryonic enzyme isoform does not lead to the "rejuvenation" of the whole organism, but a formation of some harmful, and even deadly, neoplasm.

More than just contributing to the transformation of "normal cells" into "neoplastic cells," c-Myc coordinately regulates the expression of 13 different "poor-outcome" cancer signatures [17]. In addition, functional inactivation of c-Myc in human breast cancer cells specifically inhibits distance metastasis in vivo and invasive behavior in vitro [17]. So, c-Myc may also contribute to the acquisition of metastatic capability of the "neoplastic cells."

Therefore, iPSCs generated with inducing factors including c-Myc may naturally possess some basic neoplastic features known to natural cancer cells.

The iPSCs generated without c-Myc may also possess oncogenic nature. For example, Lin28, an inducing factor used in place of c-Myc [25], has recently been found in association with cancers [72-74]. More importantly, Lin28 has been shown as a Myc-downstream factor exerting the similar effect as Myc [74-75].

iPS Reprogramming Factors and Cancer Risk

As a matter of fact, iPS reprogramming factors currently employed are more or less associated with various cancers [37-38, 76-77]. Thus, the oncogenic potential is intrinsic for iPS reprogramming, at least for the proto-type iPS reprogramming methods [39]. This intrinsic oncogenic potential is intensified when a tumor-suppressing mechanism is inhibited or knocked out [39]. Unfortunately, many iPS researchers just do not want to face this dark side of iPS reprogramming, and continue at looking at the "bright" side of their discoveries [78]. They emphasize the enhanced "efficiency" of iPS reprogramming and elevated yield of the iPSCs by knocking out the tumor-suppressing mechanisms [79-83] while ignoring the increased risks of cancer potential from these tumor suppression mechanism-jeopardized iPSCs [84-85].

Nevertheless, increasing reports are presenting observations of chromosomal aberrations [86] and cancer-related epigenome changes [87, 146] in iPSCs. There are also reports documenting formation of rhabdomyosarcomas iPSCs [88]. These observations have led to some concerns over the "variation" in the safety of iPSCs [89]. But, claims of generating "transformation-deficient" [45] and, thus, "safe-induced pluripotent stem cells" (safe-iPSCs) with therapeutic potential [46] are still being made. It has been believed that "although there are common pathways activated during reprogramming and tumorigenesis, pluripotent stem cells and tumorigenic cells have important differences" and thus the critical distinctions between true cancer cells and reprogrammed somatic cells may be that reprogrammed cells remain genetically intact" [61]. Thus, despite a clear message arguing the intrinsic distinctions between iPSCs and ESCs [90-92] and some later experimental reports supporting this argument [93-94], leading iPS researchers still reject the intrinsic distinctions between iPSCs and ESCs and the high similarity between iPSCs and cancer cells [95]. The most recent review on iPSCs still claims: "Numerous studies indicate that, at least for some clones, iPSCs are similar if not indistinguishable from ESCs derived from embryo or nuclear transfer experiments" and "somatic cells can be reprogrammed to a pluripotent state, which is molecularly and biologically indistinguishable from that of ESCs" [28] and a straight talk states that there's no reason . . . to think that true bona fide iPSCs cannot function as well as ESCs [47]. This attitude is also reflected by the lack of appreciation of the cancerous nature of iPSCs even by experienced stem cell researchers.

Amazingly, even some cancer researchers apparently still lack an understanding of the cancerous nature of the iPSCs. A recent study has found "a Myc network accounts for similarities between embryonic stem and cancer cell transcription programs" [96]. Even though some iPSCs were also included in this study, the report failed in identifying iPSCs as cancer cells. As a matter of fact, the corresponding author of this report did not even answer the straight question from the present inventor on whether or not iPSCs are cancer cells.

However, it is hoped that, continued dissection of the iPS reprogramming process may not only lead to a comprehensive identification of a sufficient factor set for complete and safe somatic to pluripotent reprogramming [97] but also an increased awareness of the neoplastic nature of iPS reprogramming [39] [125]. More importantly, if the application of this invention is placed into practice, the cancerous nature of iPSCs may be made very apparent, when anti-neoplastic agents, compounds and/or drugs discovered via methods disclosed in this application are also very effective in killing "natural cancer cells."

Genetic and Epigenetic Mutations affecting the Warburg Effect

It is important to point out that iPS reprogramming can turn "normal cells" neoplastic even without any genetic modification and/or a cell reproduction event. This feature will be a key point for the present invention which is focused on discovering anti-neoplastic agents, compounds and drugs that are effective in inhibiting the metabolic mutation serving as a root process for supporting the malicious competition of "neoplastic cells" against "normal cells." In the past, cancer research has been heavily focused on genetic mutations, including mutations in mitochondria, as causes for neoplasia [99-100]. The discovery of Warburg Effect even led some researchers to believe that neoplastic cells have abnormal mitochondria. The outcome of this genetic cancer dogma is the focus of searching anti-cancer drugs that fix the genetic mutations, including mitochondria mutations [101]. However, many drugs targeting the effects of genetic mutations often fail in killing tumor cells, and even succeed in killing normal cells [102].

It turns out that, many times, it is the mitochondrial uncoupling, the abrogation of ATP synthesis by mitochondria, promotes the Warburg Effect in some neoplastic cells and contributes to their resistance to chemotherapy targeting mitochondria [103]. These cancer cells may shift to the oxidation of non-glucose carbon sources to maintain mitochondrial integrity and function [103]. More importantly, increased level of c-Myc in cancer cells causes an increase in level of glutaminase, a protein that helps cells convert amino acid glutamine into an energy source. The breakdown of glutamine provides cancer cells with a carbon source. In fact, glutamine can serve as a major nutrient for cancer cells [104], especially when facing glucose deprivation [105]. Also worth of notice is that mutation in some genes such as KRAS or BRAF often lead to up-regulation of the expression of GLUT1 (encoding glucose transporter-1) and SGLT1 [106]. Thus neoplastic cells often have enhanced glucose uptake and glycolysis, and can survive even at low glucose concentration [107]. Thus, neoplastic cells may still have normal mitochondria despite their abnormal use. Amazingly, drugs targeting mitochondria sometimes kill normal cells more effectively, but exert less or even no harm to neoplastic cells, which use less or even shut down their mitochondria.

Metabolic Mutation/Alteration, Metabolism Switch, and Oncogenic Metabolism

A metabolic mutation or a metabolism switch may be a predominant feature in cancer cell formation. This change may happen at the epigenetic levels and this oncogenic metabolism has attracted more and more research attention recently. A simple RNA splicing which is a modification of an RNA transcript through removing of introns and joining of exons may produce different proteins out of the same gene [108-109]. This epigenetic regulation plays a very important role in normal development as well as neoplastic tumorigenesis [110-111]. Very often, the alternative splicing changes the mode of mass/energy metabolism [112-113] and this alteration in splicing can be influenced by the conditions in which the cells reside [114-115]. A very recent study just confirmed that some cancer-related epigenome changes have been found in iPSCs [87].

It should be pointed out that, although epigenetic changes have been recognized in iPS reprogramming [146], it was not until recently that mainstream journals formally recognized the "shared mechanisms" between induced pluripotency and oncogenesis [147-148]. However, these examinations often focus on the "parallels" between iPS reprogramming and cancer epigenetics in terms of the common transcription factors (TFs) used in the (iPS) "reprogramming" and the (oncogenic)"transformation" [148] but generally failed to realize the common metabolic transformation between iPS reprogramming and neoplastic transformation as discovered by the inventor of this patent application.

Evidence for Metabolic Mutation or Oncogenic Metabolism in iPSCs

Studies have shown that oncogenes such as Myc [116-117] play very important roles in contributing to glycolytic metabolism in cancer cells [70]. Studies also show that glucose deprivation induces oncogenic mutations and thus a switch to oncogenic metabolism [107]. The fact that hypoxia enhances the generation of iPSCs [118] indicates that iPSCs may have switched into a neoplastic glycolysis.

Two reports showed that butyrate promoted generation of iPSCs [149-150]. However, the promotion of iPSCs generation by butyrate was shown as c-Myc-dependent in one study [149] while the other study showed remarkable butyrate stimulation on reprogramming in the absence of KLF4 or MYC transgene [149]. The later study showed enhanced histone H acetylation, promoter DNA demethylation, and expression of endogenous pluripotency-associated gene [150].

To further support the validity of the present invention of using iPSCs for screening anti-neoplastic agents or anti-cancer drugs some additional experimental studies related to the epigenetic landscape of iPSCs [151], especially in comparison to the metabolism of cancer cells [179, 180], are described herein.

On Aug. 3, 2011, a research paper entitled "somatic oxidative bioenergetics transitions into pluripotency-dependent glycolysis to facilitate nuclear reprogramming" was published [152]. This study reported that "[T]emporal sampling demonstrated glycolytic gene potentiation prior to induction of pluripotent markers. Functional metamorphosis of somatic oxidative phosphorylation into acquired pluripotent glycolytic metabolism conformed to an embryonic-like archetype. Stimulation of glycolysis promoted, while blockade of glycolytic enzyme activity blunted, reprogramming efficiency. Metaboproteomics resolved upregulated glycolytic enzymes and downregulated electron transport chain complex I subunits underlying cell fate determination. Thus, the energetic infrastructure of somatic cells transitions into a required glycolytic metabotype to fuel induction of pluripotency." Thus, this study provided a supporting evidence for the theoretic and also logical discovery of glycolysis as a basis for the neoplastic transformation via iPS reprogramming [39, 125].

In 2012, another research article showed metabolic changes from an oxidative state to a glycolytic state during iPS reprogramming and also identified metabolites that differ between iPSCs and ESCs [153]. Interestingly, this study used an Extracellular Flux analyzer manufactured by Seahorse Bioscience (Massachusetts, United States) to measure the basal oxygen consumption rate (OCR) as a measure of mitochondrial respiration and the extracellular acidification rate (ECAR) as a measure of glycolysis-[125] More interestingly, by comparing the effects of some chemicals on the reprogramming efficiency, this study showed that a glycolysis inhibitor, 2-deoxy-D-glucose (2-DG), inhibited the reprogramming efficiency while a glycolysis stimulator, D-fructose-6-phosphate (F6P), increased reprogramming efficiency [153]. These results showed that, by using iPSCs and by measuring the effects of agents on the metabolism associated with neoplastic transformation, anti-neoplastic agents or anti-cancer drugs can be effectively identified. Unfortunately, even though the authors of this study have stated that their "study not only highlights the importance of metabolism in inducing pluripotency, but suggests that understanding the metabolic changes associated with somatic cell reprogramming may also shed light on the metabolic mechanisms regulating cancer" [153], they did not recognize iPSCs as cancer cells.

SUMMARY OF THE INVENTION

The present invention involves a discovery that "induced pluripotent stem cells" (iPS cells) are "man-made cancer stem cells" or "incorrectly programmed stem cells" that include exogenous oncogenes or oncogenic factors as a result of their "transformations" with oncogenes or oncogenic factors and, thus, are far more similar to "cancer cells" than to "embryonic stem cells," and pose a high risk of cancer to human beings and animals that receive them for cell therapy or for regenerative medicine.

The present invention provides methods for identifying (screening for) broad-spectrum anti-neoplastic drugs and agents using iPS cells (iPSCs) that have fewer side effects than chemotherapy, radiotherapy and other known cancer treatments, and that function by specifically inhibiting neoplastic cell aerobic glycolysis ("Warburg effect") and/or neoplastic cell anabolism ("pathological Cori cycle"), as well as the invasive and metastatic properties of neoplastic cells, and are harmful, preferentially, to neoplastic cells. These methods use iPS cells as replacements for naturally-occurring cancer cells and such anti-neoplastic drugs and agents in: (i) inhibiting metabolic mutation(s), which serve as a "root" for neoplastic transformations of "normal cells" into "cancer cells"; and/or (ii) killing neoplastic cells, including the iPS cells, as a result of common characteristics shared by the iPS cells with cancer cells.

The present invention also relates to a discovery that iPS cells may possess invasion and migration capabilities that are common to malignant neoplastic cells and, thus, may also be used for screening agents against the invasion, migration and metastasis of neoplastic cells.

It is an object of the present invention to use induced pluripotent stem (iPS) cells (iPSCs) for screening anti-neoplastic agents.

It is another object of the present invention to provide methods for screening agents, in single or in combination, against neoplastic cells by detecting its or their capability of inhibiting aerobic glycolysis.

It is another object of the present invention to provide methods for screening agents, in single or in combination, against neoplastic cells by detecting its or their capability of inhibiting neoplastic anabolism.

It is yet another object of the present invention to provide methods for screening agents, in single or in combination, against neoplastic cells by detecting its or their capability of inhibiting invasion, migration and metastasis.

In one aspect, the present invention comprises a method for discovering, identifying and/or screening for one or more agents, compounds and/or drugs that may potentially have a broad spectrum or other inhibitory effect on cell neoplastic activity and/or neoplastic capability (i.e., that may potentially be effective in inhibiting any and all such neoplastic activity or neoplastic capability) using one or a plurality of one or more types of induced pluripotent stem cells, wherein such neoplastic activity or neoplastic capability includes, but is not limited to, oncogenic and/or neoplastic metabolism, rapid cell growth and/or reproduction, cell invasion and/or migration, or metastasis, or any combination thereof, comprising the following steps in any suitable order:
  (a) separately or sequentially cultivating an amount of the induced pluripotent stem cells:
    (1) in a presence of one or more of the testing agents, compounds or drugs for a period of time in a culture medium that provide all necessary nutrients for the induced pluripotent stem and at an incubation temperature that is conducive for the growth and reproduction of the induced pluripotent stem (treatment group); and
    (2) in an absence of any testing agents, compounds or drugs (of step (a)(1) or otherwise) for the same, or a similar, period of time, and at the same, or a similar, temperature, as is set forth in step (a)(1) (control group);
  (b) measuring any neoplastic activity or neoplastic capability, or both, exhibited by each of the two groups of cultivated induced pluripotent stem cells of step (a) (the treatment group and the control group) to provide a set of one or more measurements for each of the two groups;
  (c) comparing the two sets of measurements obtained in step (b); and
  (d) selecting one or more of the testing agents, compounds or drugs of step (b) that has been determined to partially or fully inhibit neoplastic activity or neoplastic capability in any of the induced pluripotent stem cells of step (b) for use as a potential anti-neoplasia agent, compound or drug in human beings or animals, or both; and
  (e) optionally, additionally conducting one or more in vitro or in vivo, or both, evaluations of one or more of the testing agents, compounds or drugs selected in (d) to confirm that such testing agents, compounds and/or drugs are partially or fully effective against neoplasia or cancer (i.e., are therapeutic) in humans or animals, or both.

In another aspect, the present invention comprises a method for discovering or screening for, one or more agents, compounds or drugs that are potential therapeutic candidates against neoplasia, as being harmful to, or effective in killing, or inducing death or apoptosis of, neoplastic cells, as not being harmful to normal cells or tissues, or as not causing more than minimal (or no) side effects to a cancer patient, or providing a combination thereof (of one or more of these effects), using induced pluripotent stem cells that possess one or more neoplastic features or a cancerous nature as "replacements" for naturally-occurring cancer cells as screening agents for such agents, compounds or drugs, comprising the steps of:
  (a) confirming a presence or absence of one or more neoplastic activities and/or neoplastic capabilities of the induced pluripotent stem cells in a presence of, and in an absence of, a testing agent compound or drug having an anti-neoplastic or therapeutic potential, wherein the neoplastic activities include an abnormal proliferation or uncontrolled growth and reproduction of the induced pluripotent stem cells, poorly differentiated, highly differentiated or undifferentiated induced pluripotent stem cells, an elevated metabolic mutation into aerobic glycolysis or glycolytic neoplastic anabolism or a combination of these metabolic mutations by the induced pluripotent stem cells and the neoplastic capabilities include invasion or migration of induced pluripotent stem cells into adjacent or other tissues, or the metastasis of the induced pluripotent stem cells, or any combination of these capabilities; and
  (b) selecting a testing agent, compound or drug which inhibits or causes a reduction in one or more of the neoplastic activities and/or the neoplastic capabilities or a combination of these neoplastic features specified in step (a), and which is obviously harmful to neoplastic cells, and which is not obviously harmful to normal cells or tissues;
wherein the induced pluripotent stem cells are generated from normal somatic cells with one or more reprogramming factors having oncogenic capability.

Other aspects of the present invention are described herein.

DETAILED DESCRIPTION OF THE PREFERRED EMBODIMENTS

General Description

In a preferred embodiment, the present invention comprises a method for discovering, identifying and/or screening for one or more agents, compounds and/or drugs that may potentially have a broad spectrum or other inhibitory effect on cell neoplastic activity and/or neoplastic capability (i.e., that may potentially be effective in inhibiting any and all such neoplastic activity and/or neoplastic capability) using one or a plurality of one or more types of induced pluripotent stem cells, wherein such neoplastic activity includes, but is not limited to, oncogenic and/or neoplastic metabolism, rapid cell growth and/or reproduction and wherein such neoplastic capability includes, but is not limited to, cell invasion and/or migration, or metastasis, or any combination thereof, comprising the following steps in any suitable order:
  (a) separately or sequentially cultivating an amount of the induced pluripotent stem cells:
    (1) in a presence of one or more of the testing agents, compounds or drugs for a period of time in a culture medium that provide necessary nutrients for the induced pluripotent stem and at an incubation temperature that is conducive for the growth and reproduction of the induced pluripotent stem (treatment group); and
    (2) in an absence of any testing agents, compounds or drugs (of step (a)(1) or otherwise) for the same, or a similar, period of time, and at the same, or a similar, temperature, as is set forth in step (a)(1) (control group);
  (b) measuring any neoplastic activity or neoplastic capability, or both, exhibited by each of the two groups of cultivated induced pluripotent stem cells of step (a) (the treatment group and the control group) to provide a set of one or more measurements for each of the two groups;
  (c) comparing the two sets of measurements obtained in step (b); and
  (d) selecting one or more of the testing agents, compounds or drugs of step (b) that has been determined to partially or fully inhibit neoplastic activity or neoplastic capability in any of the induced pluripotent stem cells of step (b) for use as a potential anti-neoplasia agent, compound or drug in human beings or animals, or both; and
  (e) optionally, additionally conducting one or more in vitro or in vivo, or both, evaluations of one or more of the testing agents, compounds or drugs selected in (d) to confirm that such testing agents, compounds and/or drugs are partially or fully effective against neoplasia or cancer (i.e., are therapeutic) in humans or animals, or both.

Step (a)

The induced pluripotent stem cells that are used in step (a) may be procured from sources that are known by those having ordinary skill in the art. These sources include cell banks or culture collections which receive depositions of iPSCs and make these iPSCs available for public. These sources also include companies which produce and sell iPSCs. For example, American Type Culture Collection (ATCC) (Manassas, Va.) provides an online list of various iPSCs. These iPSCs include ATCC-DYP0250 Human Induced Pluripotent Stem Cells (ATCC® ACS-1004™), ATCC-DYS0530 Human Induced Pluripotent Stem Cells (ATCC® ACS-1013™), ATCC-DYP0730 Human Induced Pluripotent Stem Cells (ATCC® ACS-1003™), ATCC-HYR0103 Human Induced Pluripotent Stem Cells (ATCC® ACS-1007™), ATCC-DYS0100 Human Induced Pluripotent Stem Cells (ATCC® ACS-1019™), ATCC-DYP0530 Human Induced Pluripotent Stem Cells (ATCC® ACS-1014™), ATCC-DYR0530 Human Induced Pluripotent Stem Cells (ATCC® ACS-1012™), ATCC-HYS0103 Human Induced Pluripotent Stem Cells (ATCC® ACS-1020™), and ATCC-DYR0100 Human Induced Pluripotent Stem Cells (ATCC® ACS-1011™) Examples of companies which sell iPSCs include System Biosciences (Mountain View, Calif.) and Sigma-Aldrich (St. Louis, Mo.). The iPSCs currently provided by System Biosciences include protein iPSCs (piPSCs) such as SC801A-1 and SC802A-1), minicircle iPSCs (mc-iPSCs) such as SC301A-1 and SC100M-1), and viral iPSCs such as SC102A-1, SC402A-1 and SC201A-1. The iPSCs currently provided by Sigma-Aldrich include iPSCs generated in DOX-inducible, non-inducible, or polycistronic formats for both human and mouse that include iPSCs reprogrammed with original four Yamanaka factors (Oct4, Klf4, Sox2, and cMyc; OKSM) such as ST000044 and original four Thompson factors (Oct4, Sox2, Lin28, and Nanog; OSLN) such as ST000005.

The amount of the induced pluripotent stem cells that are used in step (a) will be determined according to the test to be performed and the sensitivity of the test for measuring one or more aspect of neoplastic activities and/or neoplastic capabilities as stated in step (a). In principle, the amount of cells used in the test should be enough for measuring one or more aspects of neoplastic activities and/or neoplastic capabilities as stated in step (a). Because each test and the specific method and instrumentation for measuring each aspect of the neoplastic activities and/or the neoplastic capability has its own requirement of the amount of cells to be used for the test, the rough ranges, the preferred ranges, and the best ranges of cell amount should be based on each specific test. Fortunately, this invention in general relies on some well known or even standard tests and their methods for measuring the neoplastic activities and/or the neoplastic capabilities such as the glycolysis measurement for determining the neoplastic activities with XF Extracellular Flux Analyzers produced by Seahorse Bioscience (Massachusetts, MA) and the cell migration and invasion assays for determining the neoplastic capability with Boyden Chamber Assays and Gap Closure Migration Assays provided by Cell Biolabs, Inc. (San Diego, Calif.). These methods are well known to the ordinary skilled technician in the related research fields. Thus, the specific requirement for the amount of cells to be used for a specific test of the neoplastic activities and/or the neoplastic capabilities of the induced pluripotent stem cells (iPSCs) should be determined by following the conventional rules and standards easily to be found in various research papers, or textbooks, or experimental protocols often coming with the test kits. As one example, the amount of cells that is effective for measuring the viability in the level of survival of induced pluripotent stem cells (iPSCs) by the conventional 3-(4,5)-dimethyl-2-thiazolyl)-2,5-diphenyl tetrazolium bromide (MTT) assay [200] generally ranges from about 500 cells/per well to about 5000 cells/in a 96-well plate, and preferably ranges from about 1000 cells/per well to about 4000 cells cells/per well in a 96-well plate, and more preferably ranges from about 2000 cells/per well to about 3000 cells/per well in a 96-well plate.

Any testing agent, compound and/or drug (from any source) may be used in step (a). Sources for these agents, compounds and/or drugs are known by those having ordinary skill in the art. For example, Sigma-Aldrich (St. Louis, Mo.) sells many inhibitors of aerobic glycolysis which include hexokinase inhibitors such as 3-bromopyruvic acid (3-BrPA) [also known as 3-bromopyruvate (3BP)] and 2-deoxy-D-glucose (2DG), lactate dehydrogenase (LDH) inhibitors such as sodium oxamate and gossypol from cotton seeds, pyruvate dehydrogenase kinase (PDK) inhibitors such as dehydroabietylamine, dichloroacetic acid, potassium dichloroacetate and sodium dichloroacetate. Many of these inhibitors are known for their potential values in anticancer treatment [201-204].

The amount of the testing agent, compound and/or drug that is used in step (a) will be determined according to the test to be performed and the potency of the test agent. In principle, the amount of the test agent used in the test should be enough for measuring the effect to be observed and to show a range of does-effect relationship. This does-effect range usually covers 3- to 5-log orders such, for example, from a numeric value of 1 to a numeric value of 100 (a 3-log range) or from 0.01 to 100 (a 5-log range). Because the test agents to be used for measuring their effect(s) on neoplastic activities and/or neoplastic capability of the induced pluripotent stem cells could be many kinds and thus it is impossible to list the amount of test agents for each testing agent. However, as an example, the amount of 3-bromopyruvic acid (3-BrPA), an inhibitor of hexokinase critical for aerobic glycolysis [200], generally ranges from about 0.01 uM to about 100 uM, and preferably ranges from about 0.1 uM to about 10 uM, and more preferably ranges from about 1 uM to about 5 uM.

In step (a) above, the two sets of the induced pluripotent stem cells are separately cultivated for a period of time that is effective for observing specific parameters of the neoplastic activities and/or neoplastic capabilities. The length of this time period depends on specific test and methodology and thus should be determined by consulting with the conventional protocols and standards. For the conventional 96-well plate-based MTT assay on the survival of cells treated with 3-bromopyruvic acid (3-BrPA) aerobic glycolysis [200], which generally ranges for a period of time ranging from about 12 hours to about 72 hours, and preferably ranges for a period of time ranging from about 24 hours to about 48 hours, and most preferably ranges from about 32 hours to about 36 hours.

The temperature that should be maintained during the cultivation of step (a) is a temperature that is effective for normal growth and reproduction of tissue cells, which generally ranges from about 20 to about 40° C., and preferably ranges from about 30 to about 38° C., and most preferably ranges from about 34 to about 37° C.

The media in which the two sets of induced pluripotent stem cells are cultivated may be any media that has the characteristics of supporting growth of embryonic stem cells, which are known by those having ordinary skill in the art. These media can be found in books describing the generation and cultivation of iPSCs [205-207]. Many media are available from commercial sources such as the mTeSR1 medium from Stem Cell Technologies (Vancouver, BC, Canada).

Step (b)

The measurement of separately cultivated induced pluripotent stem cells (iPSCs) are made at the same or similar time at multiple time points. The measurement of sequentially cultivated induced pluripotent stem cells (iPSCs) are made at different time points before and after the exposure to one or more testing agents, compounds or drugs. Equipment that may be used to make the measurement of step (b) is known by those having ordinary skill in the art and includes, for example, Extracellular Flux analyzers, which is available from sources that are known by those having ordinary skill in the art, such as from Seahorse Bioscience (Massachusetts, United States; http://www.seahorsebio.com/).

Step (c)

The effect of one or more testing agents, compounds or drugs on one or more selected aspects of neoplastic activities and/or neoplastic capabilities is revealed by comparing the observations on the measured parameter(s) between the treatment group and the control group. The comparison can be made between treatment group and the control group tested in parallel at the same time. Alternatively, the comparison can be made between cells before and after exposure to one or more testing agents. One way to compare the results of observations between the treatment and the control groups is to compare the half-inhibition concentration ($IC_{50}$) of an potential anti-neoplastic agent or anti-cancer drug calculated from the dose-effect curves plotted with the measurement values on the effective concentrations of the tested agent or drug over a specific aspect of the neoplastic activity or neoplastic capability.

Step (d)

Based on the comparison performed in step (c), the degree of the effect of the of one or more testing agents, compounds or drugs on one or more selected aspects of neoplastic activities and/or neoplastic capabilities can be determined from statistical analysis on the difference between the treatment and the control groups in a compared parameter such as the $IC_{50}$ described in step (c). The statistical analysis methodologies are known to the ordinary skilled technicians in the research field and are often provided with software such as SAS (Cary, N.C.). As a specific example, the survival data after the treatment with a testing agent may be analyzed with one-way ANOVA test provided in the KaleidaGraph (Reading, Pa.). The agent(s), compound(s) or drug(s) which shows statistically significant inhibition on one or more measured aspects of neoplastic activities and/or neoplastic capabilities is selected as potential anti-neoplastic agent(s), compound(s) or drug(s).

Step (e)

The potential anti-neoplastic agent(s), compound(s) or drug(s) determined in step (d) may be further evaluated with one or more in vitro tests against natural cancer cells or with one or more in vivo tests against neoplasia in animals or humans or both. These tests will further assess the anti-neoplasia or anti-cancer efficacy of the potential anti-neoplastic agent(s), compound(s) or drug(s) selected from their effective inhibition on the neoplastic activities and/or neoplastic capabilities of induced pluripotent stem cells (iPSCs) and evaluate their potential side effects and clinical safety. Well characterized natural cancer cells are available from sources that are known by those having ordinary skill in the art. For example, American Type Culture Collection (ATCC; http://www.attc.org) lists identified human tumor cells according to genetic mutations, tissue types, and molecular signatures. Standard protocols for in vivo tests in animals or humans are established and well known to the ordinary skilled technicians in the research field.

Sources of Ingredients

All of the ingredients, materials and equipment employed in the methods of the present invention are commercially available from sources that are known by those having ordinary skill in the art, such as those that are otherwise described herein, and Cell Biolabs, Inc. (San Diego, Calif.), Sciencelab.com, Inc. (Houston, Tex.), Fluka Chemical and Biochemical Co. (Ronkonkoma, N.Y.), Sony North America (New York, N.Y.), NOVA Technology Corporation (Portsmouth, N.H.), ServoMed (Sweden), (Expo Engineered Inc., Cicero, Ill.), Life Technologies (Grand Island, N.Y.), System Biosciences (Mountain View, Calif.), and Sigma-Aldrich (St. Louis, Mo.).

EXAMPLES

The examples that are set forth herein describe and illustrate the methods of the present invention. These examples are intended to be merely illustrative of the present invention, and not limiting thereof in either scope or spirit. Those having ordinary skill in the art will readily understand that variations of certain of the ingredients, amounts, conditions and/or steps employed in the procedures described in the examples can be employed.

According to the present invention, potential therapeutic agents, compounds and drugs may be screened for their ability for inhibiting aerobic glycolysis in neoplastic cells. Aerobic glycolysis has been studied for many decades now and the technical practitioners in the related research field should be familiar with the arts of how to examine the effect of various agents on the different aspects of aerobic glycolysis. Studies can be also designed to study the specific gene expression and/or the enzyme activity related to an aspect of aerobic glycolysis. There have been many publications reporting such studies and thus methodologies can be easily obtained and followed. But the Seahorse Bioscience (Massachusetts, United States) approach (http://seahorsebio.com) may provide a very convenient way to achieve these goals. The approach comprises simultaneous measurement of oxygen consumption rate (OCR) and extracellular acidification rate (ECAR) in the presence or absence of the testing compounds and, thus, determination of the rate of oxidative phosphorylation (OXPHOS) and glycolysis, respectively. A change from OXPHOS to glycolysis is usually the earliest change in the process of oncogenic transformation. On the contrary, an inhibition of glycolysis can be used as an early indicator for the anti-neoplastic potential of the testing agent.

According to the present invention, potential therapeutic agents, compounds and drugs may also be screened for their ability in reducing the competitiveness of neoplastic cells in neoplastic anabolism. Neoplastic anabolism includes two major aspects: (i) the competitive strength of neoplastic cells in grabbing and utilizing resources for cell mass production; and (ii) the existence of a pathogenic Cori cycle that provides resources to neoplasm. Any means known by those having ordinary skill in the art to measure a reduction in the competitiveness of neoplastic cells and a blockage of the pathogenic Cori cycle can be used for checking the effect of the screened agents in affecting these processes in iPSCs. For example, studies can be designed to measure the gene expression or the enzyme activity related to an aspect of neoplastic anabolism.

According to the present invention, potential therapeutic agents, compounds and drugs may be screened for their ability of inhibiting invasion, migration and/or metastasis of neoplastic cells. This kind of study has been routinely performed with other cancer cells and the methods available in published literature can be easily found and followed by those having ordinary skill in the art.

According to the present invention, potential therapeutic agents, compounds and drugs may also be screened for their ability for inducing death of neoplastic cells. There are many methods for assessing cell viability and some of them are routinely used and thus well known by those having ordinary skill in the art.

Prior arts in studying effects of agents on cancer cell metabolism, growth, reproduction, invention, and migration are abundant and very easy to find. One embodiment of carrying out the present invention of screening anti-neoplastic agents, compounds and drugs using iPSCs comprises the following steps in any suitable order:

Step 1

First, the metabolic status of iPSCs should be evaluated so that their suitability for screening different kinds of anti-neoplastic agents can be assessed and a background "control" can be established. This metabolism diagnosis can be done with a Seahorse Bioscience (Massachusetts, United States) XF Extracellular Flux Analyzer and there is rich information present on the Seahorse Bioscience (Massachusetts, United States) website (http://seahorsebio.com/products/xf-analyzers/index.php) for understanding the principles underlying the assays and learning how to perform the various tests. Successful applications revealed in scholar publications can also be found there. If the analysis shows a predominance of glycolysis in the tested cells, then not only the nature of testing cells as bona fide neoplastic cells is confirmed, but also the suitability for working as a model for screening anti-glycolysis broad spectrum anti-neoplastic agents is established.

Step 2

Secondly, the testing agents should be evaluated for their effects on the metabolism of the iPSCs. Again, this evaluation can be performed using the Seahorse Bioscience (Massachusetts, United States) XF Extracellular Flux Analyzer. If the testing agents can inhibit the glycolysis more than other aspect of the metabolism, then the chance of them serving as effective metabolic root-level anti-neoplastic agents is great and their side-effect may be minimal.

Step 3

Thirdly, the metabolic effective testing agents can be evaluated further for their capability to kill the testing cells. It is well known in the art that viability of a cell can be determined by contacting the cell with a dye and viewing it under a microscope. The most common dye used in the art for this purpose is trypan blue, which is available from Life Technologies (Grand Island, N.Y.). Viability of cells can also be determined by detecting DNA synthesis. Cells can be cultured in cell medium with labeled nucleotides, e.g., $^3$H thymidine. The uptake or incorporation of the labeled nucleotides indicates DNA synthesis. In addition, colonies formed by cells cultured in medium indicate cell growth and is another way to test viability of the cells.

Step 4

Fourthly, novel anti-neoplastic agent(s), compounds and drugs could be tested against iPSCs in tetrazolium salt-based metabolic assays such as the XTT Assay, which is available from Cell Signaling Technologies (Danvers, Mass.). As such, the respective iPSCs that are maintained and propagated in cell culture medium (e.g. RPMI 1640/10% FCS) could be plated in 96-well plates and then incubated for a given time period (e.g. 48 to 72 hours) with the respective testing agent(s), using no testing agent(s) group as a control. At the end of such incubation, XTT substance (and its activation reagent) would be added and the level of soluble formazan product derived from XTT by cellular enzymes would be measured. The more cell proliferation coinciding with metabolic activity is present, the more formazan would be produced by the cells from XTT. If however, there is an active anti-neoplastic agent, compound or drug equally (or otherwise) present, such formazan production would be significantly reduced or terminated as a result of the growth-inhibitory effect of such compound. The amount of active anti-neoplastic agent, compound or drug present typically directly correlates with the amount of reduction of formazon production, and generally ranges from about 0.01 uM to about 1000 uM, and preferably ranges from about 0.1 uM to about 100 uM, and more preferably ranges from about 1 uM to about 10 uM. Using the information that is provided herein, those having ordinary skill in the art can readily determine the most beneficial amount of active anti-neoplastic agent, compound or drug to use in a particular situation.

All of these mentioned, and many other unmentioned, cell viability/proliferation tests are well-established, and are known by those having ordinary skill in the art. Many cell viability/proliferation tests are commercially available from sources that are known by those having ordinary skill in the art, such as from Life Technologies (Grand Island, N.Y.) and Cyprotex (Watertown, Mass.).

Step 5

Fifthly, the metabolic effective testing agents can be evaluated further for their capability to inhibit the invasion and migration of iPSCs. These evaluations can be performed using equipment and techniques that are known by those having ordinary skill in the art in the field of cancer research. For example, the invasion and migration capability can be studied using a microfluidic device [119]. The effect on metastasis can be evaluated by established methods. Cell invasion assays are commercially available from sources that are known by those having ordinary skill in the art, such as Cell Biolabs, Inc. (San Diego, Calif.) and R&D Systems (Minneapolis, Minn.). Cell migration assays are also commercially available from sources that are known by those having ordinary skill in the art, such as Trevigen (Gaithersburg, Md.), Cell Biolabs, Inc. (San Diego, Calif.) and R&D Systems (Minneapolis, Minn.).

Step 6

As a sixth point, the validity of the various anti-neoplastic effects of the selected anti-neoplastic agents, compounds and/or drugs from testing with iPSCs may be confirmed by taking steps that are described herein, or conducting other known in vitro testing, with natural cancer cells that are well characterized. Although this additional test is not an intrinsic component of the present invention, it is nevertheless helpful for establishing the present invention as a trustable and reliable method for screening anti-neoplastic agents. Well characterized natural cancer cells are available from sources that are known by those having ordinary skill in the art, such as various cancel cell lines available from American Type Culture Collection (ATCC) which even lists the identified human tumor cells according to genetic mutations, tissue types, and molecular signatures.

Step 7

Finally, iPSCs could be injected in vivo into nude mice (or other mammals), subsequently observed as to whether they grow out to develop macroscopic tumors, and, if so, treated by means of novel anti-neoplastic drug candidates identified or developed using methods of the present invention, with primary tumor shrinkage (from 20% to 100%) as one of the possible endpoints for, or indicators or, drug efficacy. Such in vivo testing is well known to those having ordinary skill in the art and is described, for example, in "Animal Models in Developmental Therapeutics" [208] and other books [209-210].

Metabolic Mutation-Based Neoplastic Transformation

Further to providing the above guidelines and continuing on illuminating the neoplastic processes in iPSCs and, thus, showcase some potential applications of using iPSCs for exploring a variety of anti-neoplastic agents, compounds and drugs, some additional examples of recent discoveries on metabolic mutation-based neoplastic transformation are presented below. Methods for discovering anti-neoplastic agents described in these reports may also serve as illustrations of additional embodiments of the current invention.

It has been shown that hypoxia and oncogenic mutations drive glycolysis, with the pyruvate to lactate conversion being promoted by increased expression of lactate dehydrogenase A (LDH-A) and inactivation of pyruvate dehydrogenase. The NAD+ pool is consecutively regenerated and supports the high glycolytic flux required to produce anabolic intermediates. Glutaminolysis provides metabolic intermediates such as alpha-ketoglutarate to feed and thereby maintain the tricarboxylic acid cycle as a biosynthetic hub. Glycolysis and glutaminolysis share the capacity to generate NADPH, from the pentose phosphate pathway and through the malate conversion into pyruvate, respectively. Both pathways ultimately lead to the secretion of lactate. More than a waste product, lactate was recently identified as a major energy fuel in tumors. Lactate produced by hypoxic tumor cells may indeed diffuse and be taken up by oxygenated tumor cells. Preferential utilization of lactate for oxidative metabolism spares glucose which may in turn reach hypoxic tumor cells. Monocarboxylate transporter 1 regulates the entry of lactate into oxidative tumor cells. Its inhibition favors the switch from lactate-fuelled respiration to glycolysis and consecutively kills hypoxic tumor cells from glucose starvation. Combination with radiotherapy renders remaining cells more sensitive to irradiation, emphasizing how interference with tumor cell metabolism may complement current anticancer modalities [120]. On the other hand, increased expression and activity of LDH-A were detected in Taxol-resistant cells which showed a higher sensitivity to the specific LDH inhibitor, oxamate. Treating Taxol-resistant cells with the combination of Taxol and oxamate showed a synergistically inhibitory effect on these cancer cells by promoting apoptosis in these cells [121].

Neoplastic cells often possess different capacities than normal cells in dealing with some metabolite [106]. To eliminate lactate and to prevent cellular acidification tumor cells show up-regulation of MCT4, an $H^+$-coupled lactate transporter. In addition, the $Na^+$-coupled lactate transporter SMCT1 is silenced in cancer cells. SMCT1 also transports butyrate and pyruvate, which are inhibitors of histone deacetylases. The silencing of SMCT1 occurs in cancers of a variety of tissues. Re-expression of SMCT1 in cancer cell lines leads to growth arrest and apoptosis in the presence of butyrate or pyruvate, suggesting that the transporter may function as a tumor suppressor. Tumor cells meet their amino acid demands by inducing xCT/4F2hc, LAT1/4F2hc, ASCT2, and ATBO,+. xCT/4F2hc which is related primarily to glutathione status, protection against oxidative stress, and cell cycle progression, whereas the other three transporters are related to amino acid nutrition. Pharmacologic blockade of LAT1/4F2hc, xCT/4F2hc, or ATBO,+ leads to inhibition of cancer cell growth.

An epigenetic mechanism of the Warburg effect has been proposed [122]. Fructose-1,6-bisphosphatase-1 (FBP1), which functions to antagonize glycolysis was down-regulated through NF-kappaB pathway in Ras-transformed NIH3T3 cells. Restoration of FBP1 expression suppressed anchorage-independent growth, indicating the relevance of FBP1 down-regulation in carcinogenesis. Indeed, FBP1 was down-regulated in gastric carcinomas and gastric cancer cell lines. Restoration of FBP1 expression reduced growth and glycolysis in gastric cancer cells. Moreover, FBP1 down-regulation was reversed by pharmacological demethylation. Its promoter was hypermethylated in gastric cancer cell lines and gastric carcinomas Inhibition of NF-kappaB restored FBP1 expression, partially through demethylation of FBP1 promoter.

In 2012, a study revealed that cancer cells preferentially use reductive glutamine metabolism for lipid biosynthesis [154]. Also in 2012, a study reported that glutaminolysis, a process by which glutamine is metabolized first by glutaminase (GLS) into glutamate and then by glutamate dehydrogenase (GDH) into α-ketoglutarate (αKG), activates Rag-mTORC1 signaling [155], which plays a role in glutamine addiction in cancer cells [156]. Interestingly, in 2013, a study showed that the mTORC1 pathway stimulates glutamine metabolism and cell proliferation by repressing SIRT4 and, thus, a relationship between mTORC1, SIRT4, and cancer is also suggested [157].

The recognition of metabolic mutation as a basis for neoplasia such as cancer has been evidenced by more and more high-profile publications on oncogenic metabolism. For example, very recently, a Nature article entitled "Cancer: A metabolic metamorphosis" stated that, "The discovery of cancer-associated mutations in metabolic enzymes has fuelled the idea that altered cellular metabolism may be involved in the development of cancer" [158]. It emphasizes that acute myeloid leukemias harbour mutations in isocitrate dehydrogenases 1 or 2 (IDH1 or IDH2) that confer on the enzymes the gain-of-function ability to convert α-ketoglutarate (αKG) to (R)-2-hydroxyglutarate ((R)-2HG), which was recently shown as an "oncogenic metabolite" or, in short, "oncometabolite" that contributes to tumor development [159]. Thus, "Silencing a Metabolic Oncogene" [160] has become a focus of anti-cancer research and is evidenced by a back-to-back simultaneous reports in Science that targeted inhibition of mutant IDH2 in leukemia cells induces cellular differentiation [161] and an inhibitor of mutant IDH1 delays growth and promotes differentiation of glioma cells [162].

Thus, by discovering some oncogenic metabolism in iPS reprogramming [39, 125] that are typical for neoplastic transformation [163-167], a basis for using iPSCs for screening anti-neoplastic agents or anti-cancer drugs has been established. But many efforts are still required for convincing mainstream scientists that iPSCs are cancerous cells.

advantages of invention

Using iPSCs for screening anti-neoplastic agents/drugs has many advantages which include but are not limited to:

(1) First, there are many different types of iPSCs which are readily available for research or other use. Although the study of iPS reprogramming has a very short history and the "first-generation" iPSCs were generated only recently in 2006 the progress of iPS research has been very fast in terms of generating more and more iPSCs. A very significant factor in speeding up the iPS research is the increasing recognition of the cancer risks associated with the earlier-generated iPSCs and thus the need to overcome the shortcomings of the previous methodologies used for generating those iPSCs. Thus, within a short seven years, the generation of iPSCs has progressed from the "first-generation" of genome integration-based expression of exogenous genes [23-30], to "second-generation" of non-genome integration-based expression of exogenous genes

[213], to "third-generation" of non-gene-expression-based but protein [211]- or RNA [126, 212]-based reprogramming, and to "fourth-generation" of small-chemical compounds-based reprogramming [180]. Furthermore, even though the research on iPSCs has just started in recent time, there have been many collections and even commercial sources for iPSCs. For example, American Type Culture Collection (ATCC) (Manassas, Va.) provides an online list of various iPSCs which have been detailed in the earlier section of this application. Examples of companies which sell iPSCs include System Biosciences (Mountain View, Calif.) and Sigma-Aldrich (St. Louis, Mo.). The iPSCs currently provided by System Biosciences include protein iPSCs (piPSCs) such as SC801A-1 and SC802A-1), minicircle iPSCs (mc-iPSCs) such as SC301A-1 and SC100M-1), and viral iPSCs such as SC102A-1, SC402A-1 and SC201A-1. The iPSCs currently provided by Sigma-Aldrich include iPSCs generated in DOX-inducible, non-inducible, or polycistronic formats for both human and mouse that include iPSCs reprogrammed with original four Yamanaka factors (Oct4, Klf4, Sox2, and cMyc; OKSM) such as ST000044 and original four Thompson factors (Oct4, Sox2, Lin28, and Nanog; OSLN) such as ST000005.

(2) Secondly, many iPSCs have been well characterized in their genetic aspects, and even some epigenetic aspects, and thus further exploration on their metabolic mutation-based neoplastic changes would be more productive than testing on other less known cells.

(3) Thirdly, iPSCs have become a part of some researchers' scientific lives. These dedicated iPS researchers sitting on the iPS bandwagon would become valuable human resource in carrying out the present invention of using iPSCs as target cells for screening anti-neoplastic agents, compounds and drugs if the financial incentive is given for killing (neoplastic) iPSCs, rather than creating (therapeutic) iPSCs for use in therapy and/or regenerative medicine. Therefore, once iPS researchers realize that enhancing the efficiency for generation iPSCs is not a boosting of the immortalization, but actually an intensification of the neoplastic transformation, then these iPS researchers may be the first followers in chasing the discovery of cancerous iPSCs and become the main force using established iPSCs as surrogates for natural cancer cells to search for broad-cancer-spectrum anti-neoplastic agents, compounds and drugs. This trend is not obvious at the present time. But with the disclosure of this patent application to the public in the future, this trend will for sure to come.

Thus, with a totally unexpected and even unwelcomed discovery of iPSCs as man-made cancer cells and with a detailed presentation linking iPS reprogramming with neoplastic transformation, it is anticipated that future research on neoplasia, which include all kinds of tumors and cancers, will move into a new horizon. With the finding of anti-cancer agents, compounds and drugs that are toxic maximally or even only to neoplastic cells, and minimally or even not to normal cells, clinical treatment of neoplastic diseases may yield an unprecedented beneficial outcome in cancer research and treatment of all types of cancer, which include, but are not limited to:

breast cancer
ovarian cancer
gastric cancer
lung cancer
pancreatic cancer
uterine cancer
leukemia
brain tumor
prostate cancer Future iPS Research There has been a great resistance in advancing iPS research into this beneficial direction, especially after a Nobel Prize has been awarded to an unconvincing discovery of "mature cells can be reprogrammed to become pluripotent" [131] and an unproven claim of developmental clock-reversal dedifferentiation by iPS reprogramming [123].

iPS research is a fast-moving field that is filled with hope and also hype. There are many misunderstandings deserving correction and many disputes needing settlement. For example, the debate of the origins of iPSCs remains open [36, 168-170] despite that there are clear some clear evidences that iPSCs are most likely originated from pre-existing stem cells [171,172]. Thus, the so-called induction of pluripotent stem cells from differentiated cells may be an invalid claim and the activation of cell growth and reproduction of pre-existing stem cells may be the reality [168, 171,172]. As another example, it is arguable whether the heterogeneity or the diversity of iPSCs is only a reflection of the different degrees of reprogramming [173] or more likely a reality of the carry-over of the pre-existing differences in the differentiation status of the starting cells [36, 168].

Despite many efforts, there is no report showing generation of iPSCs with just single reprogramming factor. The simplest reprogramming factors reported for generating iPSCs consists of Oct4 and small molecules [174] and it has been shown that Oct4 links multiple epigenetic pathways to the pluripotency network [175]. It appears that a combination of different reprogramming factors, often in an appropriate stoichiometry, is required for successful reprogramming [176]. The reason for this phenomenon is unclear but it could be explained by the following hypothesis: multiple "blocks" are needed for blocking the various differentiation routes that pluripotent stem cells may take. Also multiple "fixers" are needed to fix genomes into the desired epigenomes. To understand the logical legitimacy of this hypothesis one must overcome the cell division-dominated deception in understanding cell life and appreciate a cell reproduction-based understanding of cell life, including the development of multicellular organisms from a totipotent zygote to a multi-organ body consisting of tissue cells reproduced from that zygote cell via a cascade of cell differentiation in cell reproduction [214, 215]. On the other hand, it would be easy to understand the heterogeneity of the tumor/cancer cells within even a single tumor/cancer when their multiple origins are understand for the cascade developmental process [216]. This understanding also applies to the existence of heterogeneity in iPSCs when they are generated from genetically-identical cells of the same donor.

Understanding the epigenetic changes via differentiation cell reproduction is important for realizing that iPSCs can be obtained even though the reprogramming factors are just temporarily present. However, the effect of iPS reprogramming may be permanent even if the reprogramming factors and their vectors are completely removed at a subsequent time. Thus, like constructing a new house or remodeling an old house, scaffolds may be necessary, but usually are taken away at the end. But that removal of scaffolds will not affect the already built or altered house. Some iPS researchers have claimed the elimination of the risks by removing the oncogenic factors after the reprogramming [177]. But that "safety" claim may be invalid if the removal of reprogramming factors after the formation of iPSCs does not shift the metabolism from an oncogenic state back to a normal state [178]. In this regard, it was known in 1999 that "transient excess of MYC activity can elicit genomic instability and tumorigenesis" [179].

The search for reprogramming factors may find other small-molecule compounds that do not integrate into genome, but nevertheless impact the epigenetic landscape of the genome. For example, a very recent study has shown generation of pluripotent stem cells with only small-molecule compounds [180]. The small-molecule compounds with efficient reprogramming without any previously known transcription factors include the combination of "VC6TF" composed of VPA, CHIR99021, 616452, Tranylcypromine and FSK), the combination of "VC6TFZ" which is VC6TF plus DZnep [180]. However, these small-molecule compounds-reprogrammed cells present lower lever of pluripotency marker than that shown for ESCs, indicating "incomplete reprogramming." ESC-like morphology appeared from these cells only after cultivating them in a "2i-medium" with dual inhibition of glycogen synthase kinase-3 and mitogen-activated protein kinase signaling for 28 days and these 2i-competent, ESC-like cells are called "chemically induced pluripotent stem cells" (CiPSCs) [180]. Interestingly, the reprogramming efficiency of this "chemical reprogramming" was enhanced up to 40-fold to a frequency comparable to transcription factor-induced reprogramming when a synthetic retinoic acid receptor ligand, TTNPB, was added [180]. But abnormal retinoid metabolism and retinoic acid receptor (RAR) signaling is well known in cancer formation [181].

It is interesting to notice that, as reprogramming becomes a fashion in life science, metabolic mutation is even now called as metabolic reprogramming [182]. No matter what the term is, the influence of metabolism on epigenetics and disease [183] should be objectively assessed.

In this regard, a recent "short take" article in Aging Cell [184] describes quantitative assessment of higher-order chromatin structure of the INK4/ARF locus in human senescent cells and shows the high-order chromatin structure of somatic cells (fibroblasts), senescent cells, and iPSCs as repressive compaction, active decompaction, and intermediate compaction (184). Another recent publication shows metabolic changes during cellular senescence [185]. This study reports the increased ratio of glycerophosphocholine to phosphocholine upon oncogene-induced senescence (OIS) which is in contrast with a "glycerophosphocholine-to-phosphocholine switch" well-known for tumor cells. An even more recent study shows a key role for mitochondrial gatekeeper pyruvate dehydrogenase in oncogene-induced senescence [186]. This study, thus, demonstrates pyruvate as a pivot point for oncogene-induced senescence [187]. An interesting finding of this research is that OIS is associated with increased respiration and redox stress while the abrogation of OIS results in a reversion of these processes [186]. In other words, OIS divert pyruvate more into mitochondria to enter TCA cycle and thus catabolized into $CO_2$. Suppression of OIS will keep pyruvate in the cytosol and be taken into anabolism for biosynthesis [187]. Thus, it makes even more sense to understand that disabling tumor suppressors should not be regarded as a positive achievement of increasing the reprogramming efficiency [188-190], but rather a more negative impact for increasing the neoplastic capacity of the iPSCs [191]. This is because OIS [192-193] has been conventionally regarded as a barrier to tumorigenesis [194-195] and even an anti-cancer and anti-aging mechanism [196-197]. On the other hand, c-MYC overexpression is required for continuous suppression of oncogene-induced senescence in melanoma cells [198].

It should be pointed out that the above guidelines and some examples represent just some possible applications and embodiments of the present invention. It should not be understood as limitation and boundary of the present invention. The real scope and the right of intellectual property protection should be based on the claims granted for this patent application.

References

1. Sudakin, V. and T. J. Yen, *Targeting mitosis for anti-cancer therapy*. BioDrugs, 2007. 21(4): p. 225-33.
2. Gupta, R. and R. M. Brosh, Jr., *Helicases as prospective targets for anti-cancer therapy*.
Anticancer Agents Med Chem, 2008. 8(4): p. 390-401.
3. Florea, A. M. and D. Busselberg, *Anti-cancer drugs interfere with intracellular calcium signaling*. Neurotoxicology, 2009. 30(5): p. 803-10.
4. Levin, L. A. and H. V. Danesh-Meyer, *Lost in translation: bumps in the road between bench and bedside*. JAMA, 2010. 303(15): p. 1533-4.
5. Knight, Z. A., H. Lin, and K. M. Shokat, *Targeting the cancer kinome through polypharmacology*. Nat Rev Cancer, 2010. 10(2): p. 130-7.
6. Cichowski, K. and P. A. Janne, *Drug discovery: inhibitors that activate*. Nature, 2010. 464(7287): p. 358-9.
7. Hatzivassiliou, G., et al., *RAF inhibitors prime wild-type RAF to activate the MAPK pathway and enhance growth*. Nature, 2010. 464(7287): p. 431-5.
8. Poulikakos, P. I., et al., *RAF inhibitors transactivate RAF dimers and ERK signaling in cells with wild-type BRAF*. Nature, 2010. 464(7287): p. 427-30.
9. Van Cutsem, E., et al., *Open-label phase III trial of panitumumab plus best supportive care compared with best supportive care alone in patients with chemotherapy-refractory metastatic colorectal cancer*. J Clin Oncol, 2007. 25(13): p. 1658-64.
10. Moore, M. J., et al., *Erlotinib plus gemcitabine compared with gemcitabine alone in patients with advanced pancreatic cancer: a phase III trial of the National Cancer Institute of Canada Clinical Trials Group*. J Clin Oncol, 2007. 25(15): p. 1960-6.
11. Hoag, H., *Cancer drugs should add months, not weeks, say experts*. Nat Med, 2011. 17(1): p. 7.
12. Ocana, A. and I. F. Tannock, *When are "positive" clinical trials in oncology truly positive?* J Natl Cancer Inst, 2011. 103(1): p. 16-20.
13. Thompson, C. B., *Attacking cancer at its root*. Cell, 2009. 138(6): p. 1051-4.
14. Vander Heiden, M. G., L. C. Cantley, and C. B. Thompson, *Understanding the Warburg effect: the metabolic requirements of cell proliferation*. Science, 2009. 324(5930): p. 1029-33.
15. Hsu, P. P. and D. M. Sabatini, *Cancer cell metabolism: Warburg and beyond*. Cell, 2008. 134(5): p. 703-7.
16. Tisdale, M. J., *Cachexia in cancer patients*. Nat Rev Cancer, 2002. 2(11): p. 86271.
17. Wolfer, A., et al., *MYC regulation of a "poor-prognosis" metastatic cancer cell state*. Proc Natl Acad Sci USA, 2010. 107(8): p. 3698-703.
18. Borrell, B., *How accurate are cancer cell lines?* Nature, 2010. 463(7283): p. 858.
19. Emmenegger, U. and R. S. Kerbel, *Cancer: Chemotherapy counteracted*. Nature, 2010. 468(7324): p. 637-8.
20. Labi, V., et al., *Apoptosis of leukocytes triggered by acute DNA damage promotes lymphoma formation*. Genes Dev, 2010. 24(15): p. 1602-7.

21. Michalak, E. M., et al., *Apoptosis-promoted tumorigenesis: gamma-irradiationinduced thymic lymphomagenesis requires Puma-driven leukocyte death*. Genes Dev, 2010. 24(15): p. 1608-13.

22. Gilbert, L. A. and M. T. Hemann, *DNA damage-mediated induction of a chemoresistant niche*. Cell, 2010. 143(3): p. 355-66.

23. Takahashi, K., et al., *Induction of pluripotent stem cells from adult human fibroblasts by defined factors*. Cell, 2007. 131(5): p. 861-72.

24. Takahashi, K. and S. Yamanaka, *Induction of pluripotent stem cells from mouse embryonic and adult fibroblast cultures by defined factors*. Cell, 2006. 126(4): p. 663-76.

25. Yu, J., et al., *Induced pluripotent stem cell lines derived from human somatic cells*. Science, 2007. 318(5858): p. 1917-20.

26. Okita, K., T. Ichisaka, and S. Yamanaka, *Generation of germline-competent induced pluripotent stem cells*. Nature, 2007. 448(7151): p. 313-7.

27. Park, I. H., et al., *Reprogramming of human somatic cells to pluripotency with defined factors*. Nature, 2008. 451 (7175): p. 141-6.

28. Hanna, J. H., K. Saha, and R. Jaenisch, *Pluripotency and cellular reprogramming: facts, hypotheses, unresolved issues*. Cell, 2010. 143(4): p. 508-25.

29. Park, I. H., et al., *Disease-specific induced pluripotent stem cells*. Cell, 2008. 134(5): p. 877-86.

30. Hanna, J., et al., *Treatment of sickle cell anemia mouse model with iPS cells generated from autologous skin*. Science, 2007. 318(5858): p. 1920-3.

31. Kiskinis, E. and K. Eggan, *Progress toward the clinical application of patient-specific pluripotent stem cells*. J Clin Invest, 2010. 120(1): p. 51-9.

32. Salewski, R. P., E. Eftekharpour, and M. G. Fehlings, *Are induced pluripotent stem cells the future of cell-based regenerative therapies for spinal cord injury?* J Cell Physiol, 2010. 222(3): p. 515-21.

33. Andersson, E. R. and U. Lendahl, *Regenerative medicine: a 2009 overview*. J Intern Med, 2009. 266(4): p. 303-10.

34. Lee, H., et al., *Induced pluripotent stem cells in regenerative medicine: an argument for continued research on human embryonic stem cells*. Regen Med, 2009. 4(5): p. 759-69.

35. Amabile, G. and A. Meissner, *Induced pluripotent stem cells: current progress and potential for regenerative medicine*. Trends Mol Med, 2009. 15(2): p. 59-68.

36. Liu, S. V., *iPS cells: a more critical review*. Stem Cells Dev, 2008. 17(3): p. 391-7.

37. Liu, S. V., *iPS cells are man-made cancer cells*. Logical Biology, 2008. 8: p. 1618.

38. Liu, S. V., *Further evidence that iPS cells are man-made cancer cells*. Logical Biology, 2008. 8: p. 66-68.

39. Zhang, W. K., et al., *Cancer Cell Formation by iPS Techniques: Mechanisms and Testing Approaches Logical* Biology, 2009. 9: p. 22-41.

40. Maehr, R., et al., *Generation of pluripotent stem cells from patients with type 1 diabetes*. Proc Natl Acad Sci USA, 2009. 106(37): p. 15768-73.

41. Dimos, J. T., et al., *Induced pluripotent stem cells generated from patients with ALS can be differentiated into motor neurons*. Science, 2008. 321(5893): p. 121821.

42. Webb, S., *iPS cell technology gains momentum in drug discovery*. Nat Rev Drug Discov, 2009. 8(4): p. 263-4.

43. Gunaseeli, I., et al., *Induced pluripotent stem cells as a model for accelerated patient-and disease-specific drug discovery*. Curr Med Chem, 2010. 17(8): p. 759-66.

44. Georgieva, B. P. and J. M. Love, *Human induced pluripotent stem cells: a review of the US patent landscape*. Regen Med, 2010. 5(4): p. 581-91.

45. Nakagawa, M., et al., *Promotion of direct reprogramming by transformation-deficient Myc*. Proc Natl Acad Sci USA, 2010. 107(32): p. 14152-7.

46. Tsuji, O., et al., *Therapeutic potential of appropriately evaluated safe-induced pluripotent stem cells for spinal cord injury*. Proc Natl Acad Sci USA, 2010. 107(28): p. 12704-9.

47. Daley, G., *Straight talk with . . . George Daley. Interview by Elie Dolgin*. Nat Med, 2010. 16(6): p. 624.

48. Liu, S. V., *Towards a balanced view on iPS cells*. Logical Biology, 2008. 8: p. 3238.

49. Papapetrou, E. P., et al., *Genomic safe harbors permit high beta-globin transgene expression in thalassemia induced pluripotent stem cells*. Nat Biotechnol, 2011. 29(1): p. 73-8.

50. Williams, D. A. and A. J. Thrasher, *Out of harm's way*. Nat Biotechnol, 2011. 29(1): p. 41-2.

51. Aoi, T., et al., *Generation of pluripotent stem cells from adult mouse liver and stomach cells*. Science, 2008. 321 (5889): p. 699-702.

52. Wernig, M., et al., *In vitro reprogramming of fibroblasts into a pluripotent ES-cell-like state*. Nature, 2007. 448 (7151): p. 318-24.

53. Nakagawa, M., et al., *Generation of induced pluripotent stem cells without Myc from mouse and human fibroblasts*. Nat Biotechnol, 2008. 26(1): p. 101-6.

54. Vogel, G., *Breakthrough of the year. Reprogramming cells*. Science, 2008. 322(5909): p. 1766-7.

55. Vogel, G., *Cellular reprogramming. New technique RiPS open stem cell field*. Science, 2010. 330(6001): p. 162.

56. Editors of Science, *The Runners-up: Souped-up cellular reprogramming*. Science, 2010. 330: p. 1605.

57. Yamanaka, S. and H. M. Blau, *Nuclear reprogramming to a pluripotent state by three approaches*. Nature, 2010. 465(7299): p. 704-12.

58. Nicholas, C. R. and A. R. Kriegstein, *Regenerative medicine: Cell reprogramming gets direct*. Nature, 2010. 463 (7284): p. 1031-2.

59. Zhang, J., et al., *A human iPSC model of Hutchinson Gilford Progeria reveals vascular smooth muscle and mesenchymal stem cell defects*. Cell Stem Cell, 2011. 8(1): p. 31-45.

60. Misteli, T., *HGPS-derived iPSCs for the ages*. Cell Stem Cell, 2011. 8(1): p. 4-6.

61. Daley, G. Q., *Common themes of dedifferentiation in somatic cell reprogramming and cancer*. Cold Spring Harb Symp Quant Biol, 2008. 73: p. 171-4.

62. Gaspar-Maia, A., et al., *Open chromatin in pluripotency and reprogramming*. Nat Rev Mol Cell Biol, 2011. 12(1): p. 36-47.

63. Daadi, M. M., *The common path: tumor suppression in the generation of iPS cells and cancer stem cells*. Regen Med, 2010. 5(1): p. 21-2.

64. Gao, P., et al., *c-Myc suppression of miR-23a/b enhances mitochondrial glutaminase expression and glutamine metabolism*. Nature, 2009. 458(7239): p. 762-5.

65. David, C. J., et al., *HnRNP proteins controlled by c-Myc deregulate pyruvate kinase mRNA splicing in cancer*. Nature, 2010. 463(7279): p. 364-8.

66. Yuneva, M., et al., *Deficiency in glutamine but not glucose induces MYC-dependent apoptosis in human cells*. J Cell Biol, 2007. 178(1): p. 93-105.

67. Dang, C. V., *Rethinking the Warburg effect with Myc micromanaging glutamine metabolism.* Cancer Res, 2010. 70(3): p. 859-62.
68. Christofk, H. R., et al., *The M2 splice isoform of pyruvate kinase is important for cancer metabolism and tumour growth.* Nature, 2008. 452(7184): p. 230-3.
69. Christofk, H. R., et al., *Pyruvate kinase M2 is a phosphotyrosine-binding protein.* Nature, 2008. 452(7184): p. 181-6.
70. Levine, A. J. and A. M. Puzio-Kuter, *The control of the metabolic switch in cancers by oncogenes and tumor suppressor genes.* Science, 2010. 330(6009): p. 1340-4.
71. Vander Heiden, M. G., et al., *Evidence for an alternative glycolytic pathway in rapidly proliferating cells.* Science, 2010. 329(5998): p. 1492-9.
72. West, J. A., et al., *A role for Lin28 in primordial germ-cell development and germ-cell malignancy.* Nature, 2009. 460(7257): p. 909-13.
73. Viswanathan, S. R., et al., *Lin28 promotes transformation and is associated with advanced human malignancies.* Nat Genet, 2009. 41(7): p. 843-8.
74. Viswanathan, S. R. and G. Q. Daley, *Lin28: A microRNA regulator with a macro role.* Cell, 2010. 140(4): p. 445-9.
75. Chang, T. C., et al., *Lin-28B transactivation is necessary for Myc-mediated let-7 repression and proliferation.* Proc Natl Acad Sci USA, 2009. 106(9): p. 3384-9.
76. Lu, L., et al., *Pluripotent factor lin-28 and its homologue lin-28b in epithelial ovarian cancer and their associations with disease outcomes and expression of let-7a and IGF-II.* Eur J Cancer, 2009. 45(12): p. 2212-8.
77. Godmann, M., et al., *The pluripotency transcription factor Kruppel-like factor 4 is strongly expressed in intratubular germ cell neoplasia unclassified and seminoma.* Mol Hum Reprod, 2009. 15(8): p. 479-88.
78. Krizhanovsky, V. and S. W. Lowe, *Stem cells: The promises and perils of p53.* Nature, 2009. 460(7259): p. 1085-6.
79. Hong, H., et al., *Suppression of induced pluripotent stem cell generation by the p53 p21 pathway.* Nature, 2009. 460(7259): p. 1132-5.
80. Kawamura, T., et al., *Linking the p53 tumour suppressor pathway to somatic cell reprogramming.* Nature, 2009. 460(7259): p. 1140-4.
81. Li, H., et al., *The Ink4/Arf locus is a barrier for iPS cell reprogramming.* Nature, 2009. 460(7259): p. 1136-9.
82. Marion, R. M., et al., *A p53-mediated DNA damage response limits reprogramming to ensure iPS cell genomic integrity.* Nature, 2009. 460(7259): p. 1149-53.
83. Utikal, J., et al., *Immortalization eliminates a roadblock during cellular reprogramming into iPS cells.* Nature, 2009. 460(7259): p. 1145-8.
84. Hochedlinger, K. and K. Plath, *Epigenetic reprogramming and induced pluripotency.* Development, 2009. 136(4): p. 509-23.
85. Yamanaka, S., *Ekiden to iPS Cells.* Nat Med, 2009. 15(10): p. 1145-8.
86. Mayshar, Y., et al., *Identification and classification of chromosomal aberrations in human induced pluripotent stem cells.* Cell Stem Cell, 2010. 7(4): p. 521-31.
87. Ohm, J. E., et al., *Cancer-related epigenome changes associated with reprogramming to induced pluripotent stem cells.* Cancer Res, 2010. 70(19): p. 7662-73.
88. Duinsbergen, D., et al., *Tumors originating from induced pluripotent stem cells and methods for their prevention.* Ann N Y Acad Sci, 2009. 1176: p. 197-204.
89. Miura, K., et al., *Variation in the safety of induced pluripotent stem cell lines.* Nat Biotechnol, 2009. 27(8): p. 743-5.
90. Liu, S. V., *Are iPS cells really indistinguishable from ES cells?* Logical Biology, 2007. 7: p. 66-68.
91. Liu, S. V., *Further comments on the nature of iPS cells.* Logical Biology, 2007. 7: p. 69-72.
92. Liu, S. V., *iPS cells versus ES cells.* Logical Biology, 2008. 8(2): p. 47-48.
93. Chin, M. H., et al., *Molecular analyses of human induced pluripotent stem cells and embryonic stem cells.* Cell Stem Cell, 2010. 7(2): p. 263-9.
94. Chin, M. H., et al., *Induced pluripotent stem cells and embryonic stem cells are distinguished by gene expression signatures.* Cell Stem Cell, 2009. 5(1): p. 11123.
95. Newman, A. M. and J. B. Cooper, *Lab-specific gene expression signatures in pluripotent stem cells.* Cell Stem Cell, 2010. 7(2): p. 258-62.
96. Kim, J., et al., *A Myc network accounts for similarities between embryonic stem and cancer cell transcription programs.* Cell, 2010. 143(2): p. 313-24.
97. Koche, R. P., et al., *Reprogramming factor expression initiates widespread targeted chromatin remodeling.* Cell Stem Cell, 2011. 8(1): p. 96-105.
98. Laurent, L. C., et al., *Dynamic changes in the copy number of pluripotency and cell proliferation genes in human ESCs and iPSCs during reprogramming and time in culture.* Cell Stem Cell, 2011. 8(1): p. 106-18.
99. Salas, A., et al., *A critical reassessment of the role of mitochondria in tumorigenesis.* PLoS Med, 2005. 2(11): p. e296.
100. Gogvadze, V., S. Orrenius, and B. Zhivotovsky, *Mitochondria in cancer cells: what is so special about them?* Trends Cell Biol, 2008. 18(4): p. 165-73.
101. Gogvadze, V., S. Orrenius, and B. Zhivotovsky, *Mitochondria as targets for cancer chemotherapy.* Semin Cancer Biol, 2009. 19(1): p. 57-66.
102. Gogvadze, V., B. Zhivotovsky, and S. Orrenius, *The Warburg effect and mitochondrial stability in cancer cells.* Mol Aspects Med, 2010. 31(1): p. 60-74.
103. Samudio, I., M. Fiegl, and M. Andreeff, *Mitochondrial uncoupling and the Warburg effect: molecular basis for the reprogramming of cancer cell metabolism.* Cancer Res, 2009. 69(6): p. 2163-6.
104. Bode, B. P., et al., *Molecular and functional analysis of glutamine uptake in human hepatoma and liver-derived cells.* Am J Physiol Gastrointest Liver Physiol, 2002. 283(5): p. G1062-73.
105. DeBerardinis, R. J., et al., *Beyond aerobic glycolysis: transformed cells can engage in glutamine metabolism that exceeds the requirement for protein and nucleotide synthesis.* Proc Natl Acad Sci USA, 2007. 104(49): p. 19345-50.
106. Ganapathy, V., M. Thangaraju, and P. D. Prasad, *Nutrient transporters in cancer: relevance to Warburg hypothesis and beyond.* Pharmacol Ther, 2009. 121(1): p. 29-40.
107. Yun, J., et al., *Glucose deprivation contributes to the development of KRAS pathway mutations in tumor cells.* Science, 2009. 325(5947): p. 1555-9.
108. Tilgner, H. and R. Guigo, *From chromatin to splicing: RNA processing as a total artwork.* Epigenetics, 2010. 5(3).
109. Matlin, A. J., F. Clark, and C. W. Smith, *Understanding alternative splicing: towards a cellular code.* Nat Rev Mol Cell Biol, 2005. 6(5): p. 386-98.
110. Jeyaraj, S., D. M. O'Brien, and D. S. Chandler, *MDM2 and MDM4 splicing: an integral part of the cancer spliceome.* Front Biosci, 2009. 14: p. 2647-56.
111. Fackenthal, J. D. and L. A. Godley, *Aberrant RNA splicing and its functional consequences in cancer cells.* Dis Model Mech, 2008. 1(1): p. 37-42.

112. Kim, E., A. Goren, and G. Ast, *Insights into the connection between cancer and alternative splicing.* Trends Genet, 2008. 24(1): p. 7-10.
113. Malentacchi, F., et al., *Alternative splicing variants of carbonic anhydrase IX in human non-small cell lung cancer.* Lung Cancer, 2009. 64(3): p. 271-6.
114. Hirschfeld, M., et al., *Alternative splicing of Cyr61 is regulated by hypoxia and significantly changed in breast cancer.* Cancer Res, 2009. 69(5): p. 2082-90.
115. Biamonti, G. and J. F. Caceres, Cellular stress and RNA splicing. *Trends Biochem Sci,* 2009. 34(3): p. 146-53.
116. Eilers, M. and R. N. Eisenman, *Myc's broad reach.* Genes Dev, 2008. 22(20): p. 2755-66.
117. Chang, T. C., et al., *Widespread microRNA repression by Myc contributes to tumorigenesis.* Nat Genet, 2008. 40(1): p. 43-50.
118. Yoshida, Y., et al., *Hypoxia enhances the generation of induced pluripotent stem cells.* Cell Stem Cell, 2009. 5(3): p. 237-41.
119. Irimia, D. and M. Toner, *Spontaneous migration of cancer cells under conditions of mechanical confinement.* Integr Biol (Camb), 2009. 1(8-9): p. 506-12.
120. Feron, O., *Pyruvate into lactate and back: from the Warburg effect to symbiotic energy fuel exchange in cancer cells.* Radiother Oncol, 2009. 92(3): p. 329-33.
121. Zhou, M., et al., *Warburg effect in chemosensitivity: targeting lactate dehydrogenase-A re-sensitizes taxol-resistant cancer cells to taxol.* Mol Cancer, 2010. 9: p. 33.
122. Liu, X., et al., *Warburg effect revisited: an epigenetic link between glycolysis and gastric carcinogenesis.* Oncogene, 2010. 29(3): p. 442-50.
123. Okita, K and S. Yamanaka, *Induced pluripotent cells: opportunities and challenges.* Phil. Trans. R. Soc. B., 2011, 366: p. 2198-2207.
124. Kashyap, V. et al., *Regulation of stem cell pluripotency and differentiation involves a mutual regulatory circuit of the Nanog, OCT4, and SOX2 pluripotency transcription factors with polycomb repressive complexes and stem cell microRNAs.* Stem Cells Development, 2009. 18(7), p. 1093-1108.
125. Liu, S. V., Using cells reprogrammed with oncogenic factors for screening anti-neoplastic agents. US patent application publication. US2012/0196311A1, Aug. 2, 2012.
126. MacArthur, C. C. et al., *Generation of human-induced pluripotent stem cells by a nonintegrating RNA Sendai virus vector in feeder freeor xeno-free conditions.* Stem Cell Int., 2012. Article ID 564612.
127. Warren, L. et al., *Feeder-free derivation of human induced pluripotent stem cells with messenger RNA.* Scientific Report., 2012. 2: 657.
128. Han, J. et al., *A combined epigenetic and non-genetic approach for reprogramming human somatic cells.* PLoS One. 2010. 5(8) e12297.
129. Lin, S. L. and S. Y. Ying. *Mechanism and method for generating tumor-free iPS cells using intronic microRNA miR-302 induction.* Methods Mol. Biol. 2013. 936: p 295-312.
130. Okano, H. et al., *Steps toward safe cell therapy using induced pluripotent stem cells.* Circ. Res., 2013112: p 523-533.
131. http://www.nobelprize.org/nobelprizes/medicine/laureates/2012/0104480-00001
132. http://iml.biz/iPS2012.htm
133. De Peppo, G. M. et al., Engineering bone tissue substitutes from human induced pluripotent stem cells. Proc. Natl. Sci. Acad. USA, 2013. DOI 10.1073/pnas.1301190110.
134. Doi, A. et al. *Differential methylation of tissue- and cancer-specific CpG island sjores distinguishes human induced pluripotent stem cells, embryonic stem cells and fibroblasts.* Nat. Genet., 2009. 41: p 150-153.
135. Riggs, J. W. et al., *Induced pluripotency and oncogenic transformation are related processes.* Stem Cells Development, 2013. 22(1): p. 37-50.
136. Yamanaka, S. et al., Somatic cell reprogramming by retroviral vectors encoding Oct3/4. Klf4, c-Myc and Sox2, U.S. Pat. No. 8,129,187, Mar. 6, 2012.
137. Aoi, T., et al., *Erratum: Generation of pluripotent stem cells from adult mouse liver and stomach cells.* Science 2008. 321(5889): p. 641.
138]. Aoi, T., et al., *Generation of pluripotent stem cells from adult mouse liver and stomach cells.* Science 2008. 321 (5889): p. 699-702.
139. Liu, S. V. *The Final Blow-up of the Induction and Reprogramming Claim for iPS Cells.* Logical Biology, 2008. 8: p. 57-61
140. Liu, S. V. Cancer risk may still present in episomally transformed iPSCs. Logical Biology, 2009. 9(1): p. 14-15.
141. Liu, S. V., *Understanding the Nature and Risk of Incorrectly Programmed Stem Cells (iPSCs),* Logical Biology, 2009. 9(1): p. 52-60.
142. Gutierrez-Aranda, I. et al., Human induced pluripotent stem cells develop teratoma more efficiently and faster than human embryonic stem cells regardless the site of injection. Stem Cells. 2010. 28: p. 1568-1570.
143. Yamanaka, S. et al., Selection method of induced pluripotent stem cells, US Patent application publication, US20120156684, Jun. 6, 2012
144. Yamanaka, S. et al., Method of selecting safe pluripotent stem cells, US Patent application publication, US20120171717A1, Jul. 5, 2012.
145. Liu, S. V., *Understanding iPSCs by dissecting Yamanaka's patent disclosures.* Logical Biology, 2012. 12: p. 69-72
146. Hochedlinger, K. and K. Plath. *Epigenetic reprogramming and induced pluripotency.* 2009. Development 136: p. 509-523.
147. Ohm, J. E. et al., *Cancer-related epigenome changes associated with reprogramming to induced pluripotent stem cells.* Cancer Res. 2010. 70 (19): p 7662-7673.
148. Suva, M., N. Riggi, and B. E. Bernstein. *Epigenetic reprogramming in cancer.* Science 2013. 339: p. 1567-1570.
149. Liang, G. et al., *Butyrate promotes induced pluripotent stem cell generation.* J. Biol. Chem. 2010. 285 (33): p. 25516-25521.
150. Mali, P. et al., *Butyrate greatly enhanced derivation of human induced pluripotent stem cells by promoting epigenetic remodeling and the expression of pluripotency-associated genes.* 2010. 28 94): p. 713-720.
151. Papp, B. and K. Plath, *Reprogramming to pluripotency: stepwise resetting of the epigenetic landscape.* Cell Res. 2011. 21: p. 486-501.
152. Folmes, C. D. et al., *Somatic oxidative bioenergetics transitions into pluripotency-dependent glycolysis to facilitate nuclear reprogramming.* Cell Metab. 2011. 14 (2): p. 264-271.

153. Panopoulos, A. et al., The metabolome of induced pluripotent stem cells reveals metabolic changes occurring in somatic cell reprogramming. Cell Res. 2012. 22: p. 168-177.
154. Metallo, C. M. et al., Reductive glutamine metabolism by IDH1 mediates lipogenesis under hypoxia. Nature 2012. 481: p. 380-384.
155. Duran, R. V. et al., Glutaminolysis activates Rag-mTORC1 signaling. Molecular Cell 2012. 47: p. 349-358.
156. Son, J. et al., Glutamine supports pancreatic cancer growth through a KRAS-regulated metabolic pathway. Nature 2013. 496: p. 101-105.
157. Csibi, a. et al., *The mTORCJ pathway stimulates glutamine metabolism and cell proliferation by repressing SIRT4*. Cell 2013. 153: p 80-854.
158. Krall, A. S. and Christofk, H, R, *Cancer: A metabolic metamorphosis*. Nature 2013. 496: p 38-39.
159. Losman, J, et al., *(R)-2-hydroxyglutarate is sufficient to promote leukemogenesis and its effects are reversible*. Science 2013. 339: p. 1621-1625.
160. Kim, J. and R. J. DeBerardinis. Silencing a Metabolic Oncogene. Science 2013. 340: p 558-559.
161. Wang, F. et al., Targeted inhibition of mutant IDH2 in leukemia cells induces cellular differentiation. Science 2013. 340: p. 622-626.
162. Rohle, D. et al., *An inhibitor of mutant IDHJ delays growth and promotes differentiation of glioma cells*. Science 2013. 340: p. 626-630.
163. Wise, D. R. et al. *Myc regulates a transcriptional program that stimulates mitochondrial glutaminolysis and leads to glutamine addiction*. Proc. Nat. Acad. Sci. USA 2008. 105 (48) p. 18782-18787.
164. Dang, C. V. *Glutaminolysis: Supplying carbon or nitrogen or both for cancer cells?* Cell Cycle 2010. 9 (19):p. 3884-3886.
165. Dan, C. V. *Links between metabolism and cancer*. Gene Dev. 2012. 26: p 877-890.
166. Han, J.-Q. and J. Russo. *Dysregulation of glucose transport, glycolysis, TCA cycle and glutaminolysis by oncogenes and tumor suppressors in cancer cells*. Bichimca Biophysica Acta. 2012. 1826: p 370-384.
167. Zhang, J. et al. *Metabolic regulation in pluripotent stem cells during reprogramming and self-renewal*. Cell Stem Cell. 2012. 11:p 589-595.
168. Liu. S. V. *iPS cells: stem cells induced from terminally differentiated cells or just pre-existing stem cells being detected?* Logical Biology. 2007. 7:p 63-65.
169. Trosko, J. E. Commentary: "re-programming or selecting adult stem cells?" Stem Cell Rev, 2008. 4(2): p. 81-88.
170. Cahan, P. and G. O. Daley, *Origins and implications of pluripotent stem cell variability and heterogeneity*. Nature Rev. Mol. Cell Biol., 2013. 14: p. 357-368.
171. Wakao, S. et al., *Multilineage-differentiating stress-enduring (Muse) cells are a primary source of induced pluripotent stem cells in human fibroblasts*. PNAS 2011. DOI: 10.1073/pnas.1100816108
172. Kidata, M. et al., *Muse cells and induced pluripotent stem cell: implication of the elite model*. Cell Mol. Life Sci. 2012. 69(22): p. 3739-3750.
173. Liang, G. et al., Embryonic stem cell and induced pluripotent stem cell: an epigenetic perspective. Cell Res. 2013. 23:p 49-69.
174. Li, Y. et al., *Generation of iPSCs from mouse fibroblasts with a single gene, Oct4 and small molecules*. Cell Res. 2011. 21:p. 196-204.
175. Ding, J. et al., *Oct4 links multiple epigenetic pathways to the pluripotency network*. Cell Res. 2012. 22: p. 155-167.
176. Huang, J. et al., *More synergetic cooperation of Yamanaka factors in induced pluripotent stem cells than in embryonic stem cells*. Cell Res. 2009. 19:p. 1127-1138.
177. Zou, X.-Y. et al., *Establishment of transgene free induced pluripotent stem cells reprogrammed from human stem cells of apical papilla for neural differentiation*. Stem Cell Res. Therapy, 2012. 3: 43.
178. Liu, S. V. *Understanding oncogenic iPS reprogramming and using iPSCs for screening anti-cancer drugs*. Chin. J. Cell Stem Cell, 2013. 3(2):p. 106-107.
179. Felsher, D. W. and J. M. Bishop, *Transient excess of MYC activity can elicit genomic instability and tumorigenesis*. Proc. Natl. Acad. Sci. USA 1999. 96: p. 3940-3944.
180. Hou, P. et al. *Pluripotent stem cells induced from mouse somatic cells by small-molecule compounds*. Science, 2013. DOI: 10.1126/science.1239278.
181. Tang, X.-H. and L. J. Gudas, *Retinoids, retinoic acid receptors, and cancer*. Annu Rev. Pathol. Mech. Dis., 2011.6: p. 345-364.
182. Schulze, A. and A. L. Harris, *How cancer metabolism is tuned for proliferation and vulnerable to disruption*. Nature, 2012. 491: p. 364-373.
183. Kaelin Jr., W. G. and S. L. McKnight, *Influence of metabolism on epigenetics and disease*. Cell, 2013. 153: p. 56-69.
184. Hirose, A. et al., *Quantitative assessment of higher-order chromatin structure of the INK4/ARF locus in human senescent cells*. Aging Cell, 2012. 11: p 553-556.
185. Gey, C. and K. Seeger, *Metabolic changes during cellular senescence investigated by proton NMR-spectroscopy*. Mech. Ageing Dev., 2013. 134:p 130-138.
186. Kaplon, J. et al., *A key role for mitochondrial gatekeeper pyruvate dehydrogenase in oncogene-induced senescence*. Nature, 2013. 498: pp 109-112.
187. Olenchock, B. A. and M. G. V. Heiden, *Pyruvate as a pivot point for oncogene-induced senescence*. Cell, 2013. 153: p 1429-1430.
188. Hong, H. et al., *Suppression of induced pluripotent stem cell generation by the p53-p21 pathway*. Nature, 2009. 460: p 1132-1135.
189. Marion, R. M. et al., A p53-mediated DNA damage response limits reprogramming to ensure iPS cell genomic integrity. Nature, 2009. 460: p 1149-1153.
190. Utikal, J. et al., Immortalization eliminates a roadblock during cellular reprogramming into iPS cells. Nature, 2009. 460: p 1145-1148.
191. Liu, S. V. *An April Fool's Spinning on iPS Cells*. Top Watch, 2008. 3(1): p. 18.
192. Courtois-Cox, S. et al. Many roads lead to oncogene-induced senescence. Oncogene, 2008. 27:p. 2801-2809.
193. Brag, M. et al. *Oncogene-induced senescence as an initial barrier in lymphoma development*. Nature, 2005. 436: p 660-665.
194. Collado, M. and M. Serrano, *The senescent side of tumor suppression*. Cell Cycle, 2005. 4(12):p 1772-1774.
195. Prieur, A. and D. S. Peeper, *Cellular senescence in vivo: a barrier to tumorigenesis*. Curr. Opin. Cel Biol. 2008. 20:p. 150-155.
196. Hornsby, P. J. Senesence as an anticancer mechanism. J. Clin. Oncol. 2007. 25:p 1852-1857.
197. Ohtani, N. et al. Cellular senescence: its role in tumor suppression and aging. Cancer Sci., 2009. 100: p 792-797.
198. Zhuang, D. et al., *c-MYC overexpression is required for continuous suppression of oncogene-induced senescence in melanoma cells*. Oncogene, 2008. 27(52):p. 6623-6634.
199. Liu, S. V. *On reprogramming efficiency and the origins of iPSCs*. Chin. J. Cell Stem Cell, 2012. 2(4):p. 302-303.

200. Bhardwaj, V. et al., *Glycolytic enzyme inhibitors affect pancreatic cancer survival by modulating its signaling and energetics*. Anticancer Res, 2010. 30: p. 743-750.
201. Pelicano, H. et al., *Glycolysis inhibition for anticancer treatment*. Oncogene, 2006. 25: p. 4633-4646.
202. Beneteau, M. et al., *Combination of glycolysis inhibition with chemotherapy results in an antitumor immune response*. Proc. Natl. Acad. Sci. USA, 2012. 109 (4):p. 20071-20076.
203. Nakano, A. et al., *Glycolysis inhibition inactivates ABC transporters to restore drug, sensitivity in malignant cells*. PLoS One, 2011, 6(11): e27222.
204. Matsushita, K. et al., *Glycolysis inhibitors as a potential therapeutic option to treat aggressive neuroblastoma expressing GLUT1*. J. Ped. Surgery, 2012. 47: p. 1323-1330.
205. Yildirim, S., *Induced Pluripotent Stem Cells*. Springer Verlag, 2011. ISBN-10: 1461422051, ISBN-13: 978-1461422051.
206. Lakshmipathy, U. and M. C. Vemuri (eds.) *Pluripotent Stem Cells: Methods and Protocols*. Springer, 2013. ISBN-10: 1627033475, ISBN-10: 978-1627033473.
207. Ye, K. and S. Jin (eds.) *Human Embryonic and Induced Pluripotent Stem cells: Lineage-Specific Differentiation Protocols*. Springer, 2012. ISBN-10: 1617792667, ISBN-13: 978-1617792663.
208. Khleif, S. and G. A. Curt, *Animal models in developmental therapeutics*. In *Cancer Medicine* (Bast, R. C. et al., eds.) Hamilton (ON), BC Decker, 2000.
209. Baguley, B. C. and D. J. Kerr (eds.) Anticancer Drug Development. Academic Press, 2001. ISBN-10: 0120726513 ISBN-13: 978-0120726516.
210. Neidle, S. (ed.) Cancer Drug Design and Discovery. Academic Press, 2007. ISBN-10: 0123694485 |ISBN-13: 978-0123694485.
211. Kim, D., et al., *Generation of human induced pluripotent stem cells by direct delivery of reprogramming proteins*. Cell Stem Cell, 2009. 4: p 472-476.
212. Anokye-Danso, F. et al., *Highly efficient miRNA-mediated reprogramming of mouse and human somatic cells to pluripotency*. Cell Stem Cell, 2011. 8, p 376-388.
213. Jia, F. et al., *A nonviral minicircle vector for deriving human iPS cells*. Nature Method, 2010. 7:p 197-199.
214. Liu, S. V., *Linking DNA aging with cell aging and combining genetics with epigenetics*, Logical Biology, 2005. 5: p. 61-55.
215. Liu. S. V., *A theoretical framework for understanding biotic aging from molecule to organism in multicellular life*. Logical Biology, 2005. 5: p. 109-116.
216. Zhang, W. K., et al. *Occurrence of cancer at multiple sites: Towards distinguishing multigenesis from metastasis*. Biology Direct, 2008. 3:14.

Modifications to Invention

While the present invention has been described herein with specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as described and claimed herein, and that the invention be limited only by the scope of the claims which follow, and that such claims be interpreted as broadly as is reasonable.

Books, Patents, Patent Applications, Journal Articles, other Publications and Web Sites Throughout this document, various books, patents, patent applications, journal articles, web sites and other publications have been cited. The entireties of each of these books, patents, patent applications, journal articles, web sites and other publications are hereby incorporated by reference herein.

What is claimed is:

1. A method for using induced pluripotent stem cells for discovering or screening for one or more agents, compounds or drugs that have a broad spectrum anti-neoplasia effect, the method comprising the steps of:
   (a) obtaining induced pluripotent stem cells, wherein the induced pluripotent stem cells ectopically express transcription factors Oct3/4 and Sox2, and cultivating the induced pluripotent stem cells in a presence of, and in an absence of, a plurality of testing agents, compounds or drugs; and
   (b) measuring the neoplastic capability of the induced pluripotent stem cells in the presence of, and in the absence of, the testing agents, compounds or drugs, wherein measuring the neoplastic capability is selected from the group consisting of measuring oncogenic metabolism, neoplastic metabolism, cell growth, reproduction, cell invasion, cell migration, and metastasis; and
   (c) comparing the measurement results of the treatment group of the induced pluripotent stem cells in the presence of the testing agents, compounds, or drugs with the measurement results of a control group of the same induced pluripotent stem cells in the absence of testing agents, compounds or drugs; and
   (d) selecting at least one testing agent, compound or drug that inhibits the neoplastic capability of the induced pluripotent stern cells as a potential anti-neoplasia agent, compound, or drug for further necessary evaluations needed for final confirmation of its therapeutic value wherein the testing agent, compound or drug is effective in inhibiting oncogenic metabolism, neoplastic metabolism, cell growth, reproduction, cell invasion, cell migration, or metastasis.

2. The method of claim 1 wherein the transcription factors further comprise Klf4, c-Myc, or a combination thereof.

3. The method of claim 1 wherein the transcription factors further comprise Nanog, Lin28, or a combination thereof.

4. The method of claim 1 wherein aerobic glycolysis, neoplastic anabolism, or a combination thereof is measured in step (b), and wherein selecting the at least one testing agent, compound or drug further comprises selecting a testing agent, compound or drug that inhibits aerobic glyoolysis, neoplastic anabolism, or a combination thereof.

5. The method of claim 4 wherein the measurement of aerobic glycolysis comprises measurement of activity of one or more glycolytic enzymes, or formation of one or more glyolytic metabolites, or both and wherein selecting the at least one testing agent, compound or drug further comprises selecting a testing agent, compound or drug that inhibits or decreases activity of one or more the giycolytic enzymes, reduces formation of the glycolytic metabolites or both.

6. The method of claim 4 wherein the measurement of neoplastic anabolism compreises measurement of glutaminolysis, and wherein selecting the at least one testing agent, compound or drug that inhibits neoplastic anabolism further comprises selecting a testing agent, compound or drug that inhibits glutaminolysis.

7. The method of claim 5 wherein the glycolytic enzymes include pyruvate kinase isoform 2(PKM2), lactate dehydrogenase A (LDH-A), or a combination thereof.

8. The method of claim 5 wherein the glycolytic metabolites include pyruvate, lactate, or a combination thereof.

9. The method of claim 5 wherein the formation of glycolytic metabolites is measured or determined with an assay of extracellular acidification rate (ECAR) of the induced pluripotent stem cells.

10. The method of claim 6 wherein measurement of giutaminolysis comprises measuring or determining a decrease in the activity of one or more glutaminolytic enzymes, a formation of one or more glutaminolytic metabolites or both.

11. The method of claim 10 wherein measurina or determining the decrease of the activity of one or more giutaminolytic enzymes comprises measuring or determining a decrease of an activity of glutaminase (GLS), glutamate dehydrogenase (GDH), isocitrate dehydrogenases 1 or 2 (IDH1 or IDH2), or a combination thereof.

12. The method of claim 10 wherein the glutaminolytic metabolites comprise glutamate, α-ketoglutarate (αKG), (R)-2-hydroxyglutarate ((R)-2HG), or a combination thereof.

13. The method of claim 1 wherein cell number or cell mass is measured in step (b), and wherein selecting the at least one testing agent, compound or drug that inhibits the rapid cell growth and reproduction comprises selecting a testing agent, compound or drug that causes a decrease of cell number or cell mass over time.

14. The method of claim 1 wherein cell invasion, cell migration or a combination thereof is measured in step (b), and wherein selecting the at least one testing agent, compound or drug that inhibits the neoplastic capability further comprises selecting a testing agent, compound or drug that causes a decrease of cell invasion, cell migration, or a combination thereof.

15. The method of claim 1 wherein a metastasis test or assay is measured in step (b), and wherein selecting the at least one testing agent, compound or drug further comprises selecting a testing agent, compound or drug that causes metastasis according to the metastasis test or assay.

* * * * *